(12) United States Patent
Graham et al.

(10) Patent No.: US 10,582,878 B2
(45) Date of Patent: Mar. 10, 2020

(54) SYSTEMS AND METHODS FOR PROVIDING VISUAL FEEDBACK OF TOUCH PANEL INPUT DURING MAGNETIC RESONANCE IMAGING

(71) Applicants: Sunnybrook Research Institute, Toronto (CA); Baycrest Health Sciences, Toronto (CA)

(72) Inventors: Simon James Graham, Toronto (CA); Tom A. Schweizer, Oakville (CA); Stephen Strother, Toronto (CA); Fred Tam, Toronto (CA); Mahta Karimpoor, Toronto (CA)

(73) Assignees: SUNNYBROOK RESEARCH INSTITUTE, Toronto, Ontario (CA); BAYCREST CENTRE FOR GERIATRIC CARE, Toronto, Ontario (CA)

( * ) Notice: Subject to any disclaimer, the term of this patent is extended or adjusted under 35 U.S.C. 154(b) by 978 days.

(21) Appl. No.: 14/890,018

(22) PCT Filed: May 9, 2014

(86) PCT No.: PCT/CA2014/050442
§ 371 (c)(1),
(2) Date: Nov. 9, 2015

(87) PCT Pub. No.: WO2014/179890
PCT Pub. Date: Nov. 13, 2014

(65) Prior Publication Data
US 2016/0120437 A1    May 5, 2016

Related U.S. Application Data

(60) Provisional application No. 61/821,577, filed on May 9, 2013.

(51) Int. Cl.
A61B 5/00 (2006.01)
A61B 5/055 (2006.01)
(Continued)

(52) U.S. Cl.
CPC ............ *A61B 5/055* (2013.01); *A61B 5/0042* (2013.01); *A61B 5/4064* (2013.01);
(Continued)

(58) Field of Classification Search
None
See application file for complete search history.

(56) References Cited

U.S. PATENT DOCUMENTS 5,339,813 A    8/1994 DeYoe et al.
5,546,943 A    8/1996 Gould
(Continued)

FOREIGN PATENT DOCUMENTS

WO    2009050589    4/2009
WO    2012161657    11/2012

OTHER PUBLICATIONS

TACTAPAD website, Screenshot dated May 26, 2005.
(Continued)

*Primary Examiner* — Joanne M Hoffman
(74) *Attorney, Agent, or Firm* — Hill & Schumacher

(57) ABSTRACT

Systems and methods of are disclosed for providing visual feedback to a subject during magnetic resonance imaging, where the visual feedback is associated with input provided by the subject to a magnetic resonance compatible touch panel. A video camera is employed to record video images of the interaction between the subject and the touch panel, and the video images are processed to generate a real-time video signal including a rendering of the input provided to the touch panel and the interaction between the subject's hands and the touch panel. The real-time video signal is
(Continued)

provided to the subject as visual feedback, and is displayed within a time duration that is sufficiently fast to avoid the detection of the visual feedback as an error signal with the subject's brain in relation to the sense of proprioception. A measurement of the force applied to the touch panel by the subject may be recorded and employed when rendering the real-time video. The systems and methods may be employed for a wide range of diagnostic and therapeutic procedures involving magnetic resonance imaging.

24 Claims, 13 Drawing Sheets

(51) Int. Cl.
  *G01R 33/48* (2006.01)
  *G01R 33/28* (2006.01)
  *G16H 40/63* (2018.01)
(52) U.S. Cl.
  CPC ....... *G01R 33/283* (2013.01); *G01R 33/4806* (2013.01); *A61B 2576/026* (2013.01); *G16H 40/63* (2018.01)

(56) References Cited

U.S. PATENT DOCUMENTS

| | | | |
|---|---|---|---|
| 5,805,140 A * | 9/1998 | Rosenberg | G01B 5/008 345/161 |
| 5,877,732 A | 3/1999 | Ziarati | |
| 5,882,305 A | 3/1999 | Dumoulin et al. | |
| 6,099,319 A | 8/2000 | Zaltman et al. | |
| 6,711,440 B2 * | 3/2004 | Deal | A61N 1/372 607/9 |
| 6,774,929 B1 * | 8/2004 | Kopp | A61B 5/055 345/8 |
| 7,693,702 B1 | 4/2010 | Kerner et al. | |
| 7,961,943 B1 * | 6/2011 | Zeevi | G06F 3/04883 382/173 |
| 8,005,571 B2 | 8/2011 | Sutherland et al. | |
| 8,060,181 B2 | 11/2011 | Rodriguez Ponce et al. | |
| 8,073,526 B2 | 12/2011 | Graham et al. | |
| 2003/0036714 A1 * | 2/2003 | Kuth | A61B 5/441 600/587 |
| 2005/0054910 A1 * | 3/2005 | Tremblay | A61B 5/055 600/411 |
| 2005/0273000 A1 | 12/2005 | Dinehart et al. | |
| 2005/0273017 A1 | 12/2005 | Gordon | |
| 2005/0283068 A1 | 12/2005 | Zuccolotto et al. | |
| 2006/0224761 A1 * | 10/2006 | Howarth | H04N 21/235 709/231 |
| 2007/0014355 A1 * | 1/2007 | Tsukagoshi | H04N 19/172 375/240.12 |
| 2007/0239409 A1 * | 10/2007 | Alan | G06F 17/5009 703/2 |
| 2007/0284154 A1 * | 12/2007 | Li | H04M 1/23 178/18.03 |
| 2008/0038702 A1 | 2/2008 | Choquet | |
| 2008/0181459 A1 * | 7/2008 | Martin | G06K 9/00355 382/103 |
| 2008/0200796 A1 * | 8/2008 | Graham | G01R 33/28 600/411 |
| 2009/0051667 A1 * | 2/2009 | Park | G06F 3/016 345/173 |
| 2009/0209846 A1 | 8/2009 | Bammer | |
| 2010/0027854 A1 * | 2/2010 | Chatterjee | G06F 3/016 382/124 |
| 2010/0134408 A1 * | 6/2010 | Palsbo | G06F 3/011 345/156 |
| 2011/0092805 A1 | 4/2011 | Estevez | |
| 2011/0230755 A1 | 9/2011 | MacFarlane et al. | |
| 2011/0270074 A1 * | 11/2011 | deCharms | A61B 5/055 600/410 |
| 2012/0108909 A1 | 5/2012 | Slobounov et al. | |
| 2012/0249587 A1 | 10/2012 | Anderson et al. | |
| 2012/0320178 A1 | 12/2012 | Siegert et al. | |
| 2013/0006095 A1 | 1/2013 | Jenkins et al. | |
| 2014/0088941 A1 * | 3/2014 | Banerjee | G06F 3/011 703/11 |

OTHER PUBLICATIONS

Gentile et al., J Neurophysiol 105: 910-922, 2011.
Tam et al., "A new tablet for writing and drawing during functional MRI", Human Brain Mapping, vol. 32 No. 2 pp. 240-248. Feb. 2011 (Feb. 2011).
Mraz et al. "An fMRI-Compatible Writing Device for Investigation the Neural Substrates of Drawing, Copying and Tracing", Proceedings of the International society for Magnetic Resonance in Medicine, vol. 12, p. 1042, May 21, 2004 (May 21, 2004).
International search report PCT/CA2014/050442 dated Sep. 19, 2014.
Written Opinion PCT/CA2014/050442 dated Sep. 19, 2014.
Ogawa, S., Lee, T. M., Kay, A. R., & Tank, D. W. Brain magnetic resonance imaging with contrast dependent on blood oxygenation. Proceedings of the National Academy of Sciences United States of America, 1990 87, 9868-9872.
Ogawa, S., Tank, D. W., Menon, R., Ellermann, J. M., Kim, S. G., Merkle, H., & Ugurbil, K. Intrinsic signal changes accompanying sensory stimulation: functional brain mapping with magnetic resonance imaging. Proceedings of the National Academy of Sciences United States of America, 1992 89(13), 5951-5955.
Werner, P., Rosenblum, S., Bar-On, G., Heinik, J., & Korczyn, A. Handwriting process variables discriminating mild Alzheimer' disease and mild cognitive impairment. The Journals of Gerontology. Series B, Psychological Sciences and Social Sciences. 2006 61, p. 228-236.
Reisman, J. Development and reliability of the research version of the Minnesota Handwriting Test. Physical & Occupational Therapy in Pediatrics. 1993 13(2), 41-55.
Rosenblum, S., Weiss, P., & Parush, S. Product and process evaluation of handwriting difficulties. Educational Psychology Review. 2003 15(1), 41-81.
Michael P. Caligiuri, Hans-Leo Teulings, J. Vincent Filoteo, David Song, James B. Lohr, Quantitative measurement of handwriting in the assessment of drug-induced parkinsonism, Human Movement Science, vol. 25, Issues 4-5, Oct. 2006, pp. 510-522, ISSN 0167-9457, 10.1016/j.humov.2006.02.004.
Slavin, M. J., Phillips, J. G., Bradshaw, J. L., Hall, K A. and Presnell, I. Consistency of handwriting movements in dementia of the Alzheimer's type: a comparison with Huntington's and Parkinson's diseases. Journal of the International Neuropsychological Society. 1999 5, 20-55.
Schroter, A., Mergl, R., Burger, K., Hampel, H., Moller, H. J. and Hererl, U. Kinematic analysis of handwriting movements in patients with Alzheimer's disease, mild cognitive impairment, depression and healthy subjects. Dementia and Geriatric Cognitive Disorders. 2003 15, 132-142.
Cummings JL, Benson DF, Hill MA, Read S: Aphasia in dementia of the Alzheimer type. Neurology 1985; 35:394-397.
Labarge E, Smith DS, Dick L, Storandt M: Agraphia in dementia of the Alzheimer type, Arch Neurol 1992;49:1151-1156.
Ghilardi MF, Alberoni M, Marelli S, Rossi M, Franceschi M, Ghez C, Fazio F. Impaired movement control in Alzheimer's disease. Neurosci Lett. Jan. 22, 1999;260(1):45-8.
Ghilardi MF, Alberoni M, Rossi M, Franceschi M, Mariani C, Fazio F. Visual feedback has differential effects on reaching movements in Parkinson's and Alzheimer's disease. Brain Res. Sep. 8, 2000 ;876(1-2):112-23.
Snyder LH. Coordinate transformations for eye and arm movements in the brain. Curr Opin Neurobiol. Dec. 2000;10(6):747-54.
Graziano MS. Where is my arm? The relative role of vision and proprioception in the neuronal representation of limb position. Proc Natl Acad Sci U S A. Aug. 31, 1999;96(18):10418-21.

(56) References Cited

OTHER PUBLICATIONS

Newport R, Hindle JV, Jackson SR. Links between vision and somatosensation. Vision can improve the felt position of the unseen hand. Curr Biol. Jun. 26, 2001;11(12):975-80.
Taylor-Clarke M, Kennett S, Haggard P. Persistence of visual-tactile enhancement in humans. Neurosci Lett. Jan. 2, 2004;354(1):22-5.
Taylor-Clarke M, Kennett S, Haggard P. Vision modulates somatosensory cortical processing. Curr Biol. Feb. 5, 2002;12(3):233-6.
Tam F, Churchill NW, Strother SC, Graham SJ. A New Tablet for Writing and Drawing During Functional MRI. Hum Brain Mapp 2011 32: 240-248.
Zakzanis KK, Mraz R, Graham SJ. An fMRI study of the trail making test. Neuropsychologia. 2005 43:1878-1886.
Ferber S, Mraz R, Baker N, Graham SJ. Shared and differential neural substrates of copying versus drawing: A functional magnetic resonance imaging study. NeuroReport 2007 18:1089-1093.
Callaert, D.V., Vercauteren, K., Peeters, R., Tam, F., Graham, S., Swinnen, S.P., Sunaert, S., Wenderoth, N., 2011. Hemispheric asymmetries of motor versus nonmotor processes during (visuo) motor control. Hum Brain Mapp 32, 1311-1329.
Ellamil M, Dobson C, Beeman M, Christoff K. Evaluative and generative modes of thought during the creative process. Neuroimage. Jan. 16, 2012;59(2)1783-94. Epub Aug. 11, 2011.
Churchill NW, Oder A, Abdi H, Tam F, Lee W, Thomas C, Ween JE, Graham SJ, Strother SC. Optimizing preprocessing and analysis pipelines for single-subject fMRI. I. Standard temporal motion and physiological noise correction methods. Hum Brain Mapp. Mar. 2012;33(3):609-27.
Solina Franc, Peer Peter, Borut Batagelj, Juvan Samo, Kova Jure,"Color-Based Face Detection in the "15 Seconds of Fame" Art Installation", Program Computer Vision, 2003, 1539-506.
Kovac, P. Peer, and F. Solina, "Human skin color clustering for face detection," in EUROCON 2003. Computer as a Tool. The IEEE Region 8, vol. 2, pp. 144-148 vol. 2, Sep. 2003.
Macintosh BJ, McIlroy WE, Mraz R, Staines WR, Black SE, Graham SJ. Electrodermal recording and fMRI to inform sensorimotor recovery in stroke patients. Neurorehabil Neural Repair. Nov.-Dec. 2008;22(6):728-36.
Glover GH, Law CS. Spiral-in/out Bold fMRI for increased SNR and reduced susceptibility artifacts. Magn Reson Med. Sep. 2001;46(3):515-22.
Cox RW. AFNI: software for analysis and visualization of functional magnetic resonance neuroimages. Comput Biomed Res. Jun. 1996;29(3):162-73.
Glover GH, Li TQ, Ress D. Image-based method for retrospective correction of physiological motion effects in fMRI: RETROICOR. Magn Reson Med. Jul. 2000;44(1)162-7.
KJ Friston, J. Ashburner, CD Frith, J.-B. Poline, JD Heather and RSJ Frackowiak, Spatial registration and normalization of images. Hum. Brain Map. 2 (1995), pp. 165-189.
Genovese CR, Lazar NA, Nichols T. Thresholding of statistical maps in functional neuroimaging using the false discovery rate. Neuroimage. Apr. 2002;15(4):870-8.
Paweena, U., et al., International journal of computer assisted radiology and surgery 8.3 (2013): 365-378.
Fritz, Jan, et al., Radiology 265.1 (2012): 254-259.
Wang, A., et al., Computer Aided Surgery 16.4 (2011): 149-160.
Ogawa, Kenji, and Toshio Inui., Journal of cognitive neuroscience 24.1 (2012): 171-182.
Chen, Qi, et al., Journal of cognitive neuroscience 24.11 (2012): 2223-2236.
Bernier, Pierre-Michel, and Scott T. Grafton., Neuron 68.4 (2010): 776-788.
O'Dhaniel, A., Yale E. Cohen, and Jennifer M. Groh., Cerebral Cortex 19.8 (2009): 1761-1775.
Kenner et al., Neuropsychologia 47 (2009) 3105-3110.
Nahab et al., Cerebral Cortex Jan. 2011; 21:48-55.
Seidler et al., NeuroImage 22 (2004) 1775-1783.
Ku et al., NeuroImage 43 (2008) 793-800.
Naito et al., J. Neurosci, 2006, 26(14):3783-3790.
Kontaris et al., Neuropsychologia 47 (2009) 3118-31243.
Malik et al., ICMI '04 Proceedings of the 6th international conference on Multimodal interfaces, 2004.
David et al., Frontiers in Psych. 2, 1-8, 2011.
Han et al., OzCHI '12 Proceedings of the 24th Australian Computer-Human Interaction Conference, 2012.
Leube et al., NeuroImage 20 (2003) 2084-2090.
Shimada et al., PLoS One 4, 2009, e6185-1-5.
Ehrsson et al., Science 305, 2004, 875-877.

* cited by examiner

With VFHPWithout VFHP

Pre-treatment  Post-treatment

SYSTEMS AND METHODS FOR PROVIDING VISUAL FEEDBACK OF TOUCH PANEL INPUT DURING MAGNETIC RESONANCE IMAGING

CROSS-REFERENCE TO RELATED APPLICATION

This application is a National Phase application claiming the benefit of the international PCT Patent Application No. PCT/CA2014/050442, filed on May 9, 2014, in English, which claims priority to U.S. Provisional Application No. 61/821,577, titled "SYSTEMS AND METHODS FOR PROVIDING VISUAL FEEDBACK OF TOUCH PANEL INPUT DURING MAGNETIC RESONANCE IMAGING" and filed on May 9, 2013, the entire contents of which are incorporated herein by reference.

BACKGROUND

The present disclosure relates to magnetic resonance imaging (MRI). More particularly, the present disclosure relates to the use of a touch panel by a healthy subject or a patient for providing input during magnetic resonance imaging, such as functional magnetic resonance imaging (fMRI). The present disclosure also relates to use of a touch panel by a patient for providing input prior, during, and after therapeutic interventions that are guided and monitored by MRI.

Neuropsychological tests are behavioural tasks that are designed specifically to measure mental processes that are thought to be linked with one or more specific brain structures. In practice, neuropsychological tests probe various aspects of human cognition, ability, or skill, with the intent to detect abnormal brain function, and to distinguish abnormal from normal brain function. The behavioural abnormalities measured by neuropsychological tests may indicate neuropathologies such as a stroke, brain tumor, traumatic brain injury or Alzheimer's disease, and may assist clinicians to identify a treatment target and a treatment plan.

However, the relationship between task performance and neuropathology is complex, partly because the underlying brain activity is regionally distributed. This causes neuropsychological tests to be less specific than is desirable because impaired behavioral performance can occur due to damage accrued by one or more nodes in the network, or by their interconnections. One way to improve the specificity of neuropsychological tests involves simultaneous measurement of behaviour and brain activity, for example using fMRI. The fMRI method is widely recognized as a safe, non-invasive method to probe neuronal activity indirectly through the associated localized changes in blood oxygenation, flow, and volume.

Various devices for stimulus presentation and response recording are used as part of behavioural task design in fMRI. For example, a button box is commonly used to record finger press responses (e.g. "yes" or "no") to behavioural tasks. U.S. Pat. No. 8,073,526, issued to Graham et al., discloses an MRI-compatible tablet for recording drawing and writing movements during fMRI of brain activity. The system includes a touch-sensitive tablet, an elevated mounting platform, a stylus, and a controller box, as well as the necessary cabling and software.

In addition, as MRI technology advances, the imaging modality has become increasingly used in interventional applications to treat patients with brain impairment during minimally- or non-invasive procedures in which MRI provides guidance and monitoring capabilities. These procedures are advantageous because they potentially enable use of a smaller surgical field than achievable in conventional neurosurgery, as well as enhanced targeting of the treatment volume and surrounding normal tissues. Enhanced outcomes are possible while minimizing side-effects, as well as more efficient surgical procedures that minimize procedure time, shorten hospital stays, and improve socio-economic factors such as health care costs, economic productivity through faster return to work, and improved quality of life. Examples of such MRI-guided interventions include neurosurgical resection of abnormal brain tissue, either manually or using specially-designed robotics; thermal therapies using high-intensity focused ultrasound (HIFU), laser, radiofrequency, microwave, or cryogenic devices to ablate focal regions of tissue through temperature elevation or reduction; localized drug administration, either using an inserted localized delivery device or by an injectable agent that is locally activated through focal activation using ultrasound and microbubbles; and implantation of electrodes in precisely targeted brain regions to modulate the excitability or inhibitory capacity of specific neuronal populations in abnormal neural networks.

SUMMARY

Systems and methods of are disclosed for providing visual feedback to a subject (or patient) during magnetic resonance imaging, where the visual feedback is associated with input provided by the subject to a magnetic resonance compatible touch panel. A video camera is employed to record video images of the interaction between the subject and the touch panel, and the video images are processed to generate a real-time video signal including a rendering of the input provided to the touch panel and the interaction between the subject's hands and the touch panel. The real-time video signal is provided to the subject as visual feedback, and is displayed within a time duration that is sufficiently fast to avoid the detection of the visual feedback as an error signal with the subject's brain in relation to the sense of proprioception. A measurement of the force applied to the touch panel by the subject may be recorded and employed when rendering the real-time video. The systems and methods may be employed for a wide range of diagnostic and therapeutic procedures involving magnetic resonance imaging.

Accordingly, in one aspect, there is provided a method of providing visual feedback to a subject during magnetic resonance imaging, wherein the visual feedback is associated with input provided to a touch panel, the method comprising:

recording input provided by the subject to a magnetic resonance imaging compatible touch panel while the subject is positioned within a magnetic resonance imaging scanner;

recording images of the interaction between the subject and the touch panel, such that the images include one or more of the subject's hands;

processing the images and the input provided to the touch panel to generate a real-time video signal comprising:

a rendering of the input provided to the touch panel by the subject; and an image of the one or more hands, showing the real-time position of the one or more hands; and displaying the real-time video signal to the subject in real time;

wherein the real-time video signal is rendered, relative to the recording of the images within a time duration that is sufficiently fast to avoid the detection of the visual feedback as an error signal with the subject's brain in relation to the sense of proprioception.

In another aspect, there is provided a system for providing visual feedback to a subject during functional magnetic resonance imaging, the apparatus comprising:

a magnetic resonance imaging compatible touch panel configured to receive input from the subject;

an imaging device positioned and oriented to record images of the interaction between the subject and the touch panel, such that the images include one or more of the subject's hands;

a display device configured to display visual feedback to the subject of the input provided to the touch panel;

a processor operatively coupled to said imaging device and said touch panel, wherein said processor is configured to:

record input provided by the subject to said magnetic resonance imaging compatible touch panel while the subject is positioned within a magnetic resonance imaging scanner;

record images obtained by said imaging device of the interaction between the subject and said touch panel, such that the images include one or more of the subject's hands;

process the images and the input provided to said touch panel to generate a real-time video signal comprising:
a rendering of the input provided to the touch panel by the subject; and
an image of the one or more hands, showing the real-time position of the one or more hands; and display the real-time video signal to the subject on said display device;

wherein the real-time video signal is rendered, relative to the recording of the images within a time duration that is sufficiently fast to avoid the detection of the visual feedback as an error signal with the subject's brain in relation to the sense of proprioception.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 7A illustrates difficulty level 1, during which the location of one symbol must be remembered. FIG. 7B illustrates difficulty level 2, during which the location of two symbols must be remembered.

DETAILED DESCRIPTION

Figure 1:
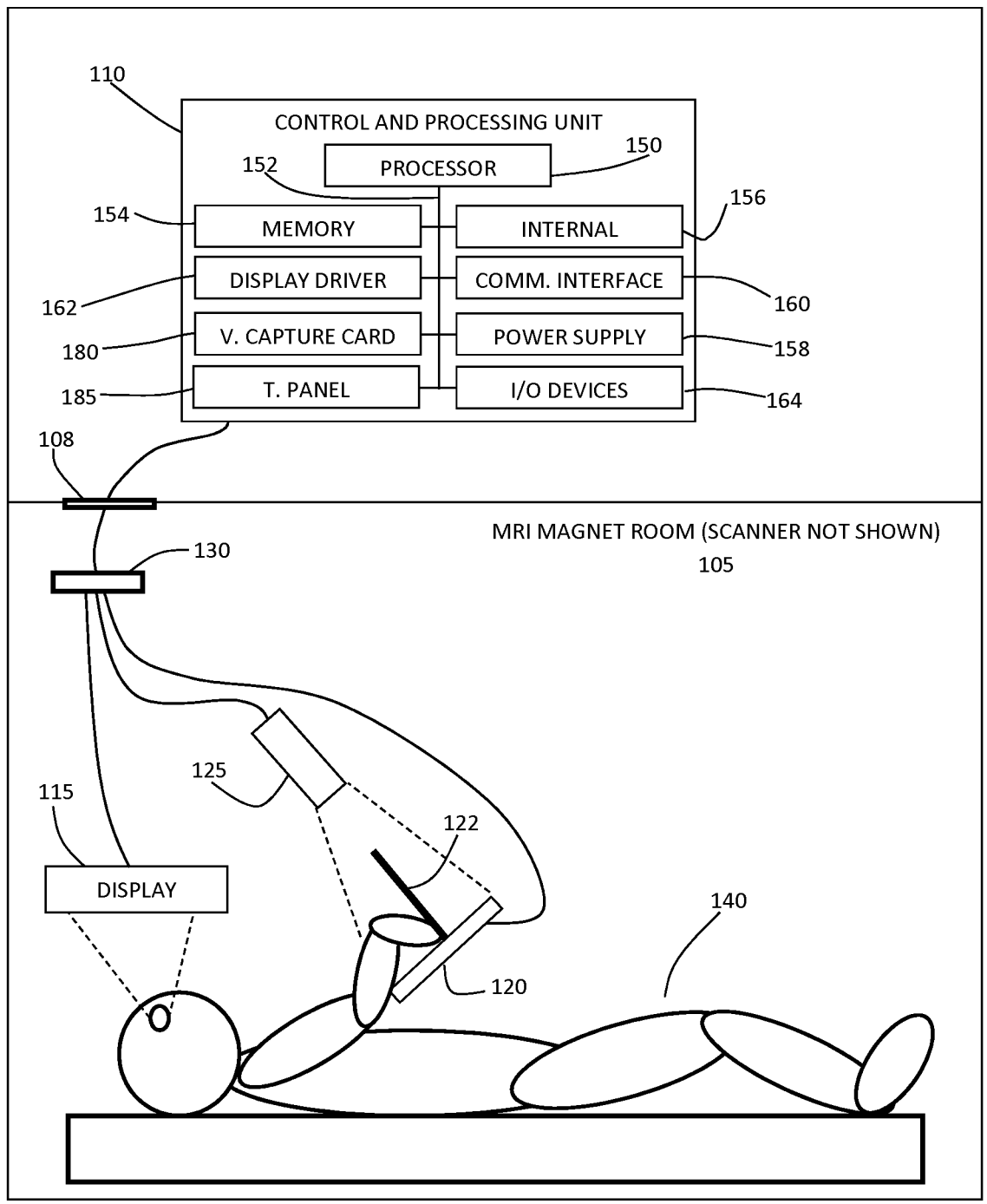
FIG. 1 shows a block diagram of an example system for performing fMRI based on input from a touch panel, where the system is configured for providing visual feedback of the subject's hands in real-time.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

The term "touch," as used herein, may refer to a touch of an object, such as a body part (e.g., a finger) or a pointing device (e.g., a soft stylus, pen, etc.). A touch may be deemed to have occurred if a touch panel detects a touch, by virtue of the proximity of the object to the sensor, even if physical contact has not occurred.

As used herein, the term "touch panel" generally refers to a touch-sensitive device that provides a signal identifying the position on the panel where an object contacts the panel. In some embodiments, a touch panel may provide a signal indicative of when a finger or object is in close proximity to the panel (e.g., a capacitive panel or a near field panel). The touch panel may optionally be integrated with a display screen.

As used herein, the phrase "force sensor" refers to a tactile sensor, such as a pressure sensor, that is configured to provide a signal that is related to the amount of applied force or pressure, over a range of values of applied force or pressure, as opposed to a microswitch or binary sensor that only registers a signal when an applied force or pressure exceeds a pre-selected threshold. In some embodiments, a force sensor provides an output signal that is proportional to the amount of applied force or applied pressure. In some embodiments, a force sensor may reside within a stylus, such that a signal associated with the amount of applied force or applied pressure is provided by the sensor within the stylus. In other embodiments, the touch panel may include one or more force sensors such that the amount of applied force or pressure is measurable by the touch panel instead of by a force-sensing stylus.

As used herein, the phrase "MRI compatible" refers to a device formed from a non-ferromagnetic materials that may be used within an MRI scanner. An example of a non-ferromagnetic material is plastic, which prevents attractive forces between the device and the superconducting magnet of the MRI scanner. MRI-compatible devices may be interfaced with external electronics through shielded electrical cables to eliminate electromagnetic interference that could corrupt the data measured by the device, and/or corrupt the signal-to-noise ratio or contrast-to-noise ratio of MRI and/or fMRI data.

As used herein, the phrase "real time" refers to the display of images containing information associated with the motion of a subject, where the images are displayed with a time delay that is sufficiently small to avoid the detection, by the subject, of the visual feedback as an error signal with the subject's brain in relation to the sense of proprioception.

Embodiments of the present disclosure provide systems, devices and methods for receiving subject input on a touch panel during functional magnetic resonance imaging (fMRI), where visual feedback is provided to the subject in a manner that facilitates input when the touch panel and the subject's hands are not directly visible to the subject.

An attempt to provide such feedback to a subject during fMRI was made by Graham et al. in U.S. Pat. No. 8,073,526.

In Graham et al., an MRI-compatible tablet is positioned within the bore of a MRI scanner, such that the subject may provide input and/or complete tasks during imaging. The subject interacts with the tablet during fMRI via a stylus. The tablet is accessible to the hands of the subject, but due to the supine orientation of the subject, neither the subject's hands, nor the tablet, nor the stylus, are visible to the subject. A projection display (or MRI-compatible goggles) is employed to display drawing motions made by the subject via contact between the stylus and the tablet, and/or any visual stimuli that are presented to the subject for the purpose of assessing specific aspects of human behaviour.

In U.S. Pat. No. 8,073,526, Graham et al. acknowledge that the inability of the subject to view his or her hands when providing input to the tablet can lead to problems with usability. In an attempt to overcome this problem, the system of Graham et al. is configured to display a crosshair when light contact is made between the stylus and the tablet, i.e. when contact is made such that the applied pressure is below a predetermined threshold. This allows the user to identify the location of contact, without entering input. A microswitch is integrated into the stylus tip that senses when the amount of pressure exceeds the threshold. When this threshold is exceeded, the active position of the cursor is moved to the location of contact. Accordingly, a subject residing within the bore of the MRI may provide input in the form of drawing or handwriting by the following process: lightly contacting the stylus with the tablet to identify the initial location of the stylus; moving the stylus to position the crosshair to a desired initial location; applying sufficient pressure to trigger the microswitch; and moving the stylus to produce the desired writing or drawing input.

Unfortunately, the present inventors have determined, through clinical investigations, that the crosshair/microswitch input method disclosed in U.S. Pat. No. 8,073,526 presents difficulties for the subject due to the substantial differences between the crosshair/microswitch guided input method and that of conventional writing. In particular, the crosshair/microswitch input method does not provide sufficient feedback to support the hand-eye coordination skills needed for efficient and accurate handwriting and drawing, thus precluding the use of a touch panel in a manner that is similar to natural writing and drawing behaviour. In other words, the crosshair/microswitch input method fails to capture ecologically valid input behaviour, i.e. behaviour that is representative of the real-world performance of the task in a typical setting outside of the MRI bore.

In the context of fMRI, when recording maps of brain activity, it is such ecologically valid activation patterns that are desired—i.e. activation patterns that reflect the nature of the human subject or subject as they write and draw, rather than activation patterns which are strongly influenced by the tool that they are using. This is important because the use of a touch panel is intended to facilitate the ecologically valid (natural) input, rather than making it more difficult and unnatural for the subject to provide input. This is especially relevant for subjects suffering from cognitive impairments, such as Alzheimer's disease subjects or subjects with traumatic brain injury, for which the crosshair/microswitch method can be problematic. For such a subject that is impaired according to a particular neuropsychological test, a particular pattern of brain activity should be interpreted and evaluated based on the brain activity associated with the neuropsychological test, and not confounded by the manner in which they provide input through a touch panel.

An additional limitation of the crosshair/microswitch input method is that the method makes it difficult for subjects, after periods of rest, to determine where to initiate writing and drawing on the touch panel. For example, if subjects have to initially start writing within a prescribed field on the screen in a certain location, they must first lightly contact the stylus with the tablet to identify an initial location, and then move the stylus to the desired location for providing input. In other words, the subject is prevented from moving directly to the desired location on the tablet. This complexity and inefficiency can be frustrating and confusing for the subject, and also affects response time and accuracy. This may especially true if the movement is required to be brief and targeted (for example, to touch within a small box). It is therefore apparent that the indirect nature of the crosshair/microswitch input method impairs the ecological validity of the resulting fMRI data.

The present inventors have determined that the absence of the visibility of the subject's hands, and the reliance on a binary-level sensor for initiating input, leads to poor coordination, causing the input process to be complex and confusing—and therefore not sufficiently ecologically valid. Accordingly, as described in one embodiment of the present disclosure, the process of a subject providing input to a touch panel during fMRI can be improved by providing the subject with (i) real-time visual feedback of the user's hand position relative to the touch panel and, optionally (ii) real-time feedback of the level of applied force between the stylus (or finger) and the touch panel. This may be achieved, for example, using an MRI-compatible camera to obtain video images of the subject's hands, such that images of the hands can be segmented and superimposed with touch panel performance image data in an augmented reality display.

The methods, devices and systems described in the example embodiments provided below, in which improved visual feedback is provided to the subject during use of the touch panel, may be beneficial in applications in which fMRI is employed to provide a marker of normal or baseline brain function in healthy individuals and in patients. The embodiments also may be beneficial in relation to qualitative or quantitative behavioural monitoring of a patient throughout aspects of an ongoing interventional procedure that is occurring during any or all forms of MRI within an MRI scanner, as it can be important in such applications to ensure that the behavioural performance associated with the input from the touch panel is ecologically valid. This may include, for example, imaging sessions for planning the therapeutic intervention, as well as for evaluating therapeutic response or outcome in the days, weeks, and months after the therapeutic intervention.

Unlike the aforementioned crosshair/microswitch input method, the embodiments disclosed herein employing visual feedback of hand position and contact force enable the subject to provide input directly and unambiguously, without having to first establish an initial position by making contact with the touch panel. The direct nature of the input process, with improved efficiency and accuracy, may provide both an improved experience for the subject and input that is more ecologically valid for fMRI studies. Furthermore, the visual feedback methods disclosed herein could reduce the amount of time that is needed for the subject to learn and adapt to using the tablet, particularly in the case where the patient has a neurological disorder. This may be helpful in preventing artifacts in activation maps that are due to improper on incomplete learning.

Referring now to FIG. 1, a system diagram of an example embodiment is illustrated, where a control and processing unit 110, located in control room 100 is interfaced through a penetration panel 108 with a display device 115, a touch panel 120, and a video camera 125 located in the MRI magnet room 105. Video camera 125 is oriented to record video images of the touch panel, including the subject's hands.

Control and processing unit 110 processes the video images obtained by video camera 125 to segment and extract the subject's hands from the video images, and to superimpose a rendering of the subject's hands (and optionally a stylus) with input and/or task-related video image data presented to the user. Display 115 is positioned (optionally with projection screens and/or mirrors), such that the superimposed image is observable by subject 140. In some embodiments, subject 140 may provide input to touch panel 120 via stylus 122, which may be a passive stylus or an active stylus that is interfaced with control and processing unit 110.

In one example implementation, the touch panel 120 may be an MRI-compatible tablet, as described in U.S. Pat. No. 8,073,526. The illustrated design described in this patent employed a 6.4" by 6.4" polyester laminate (PL) resistive 4-wire touch panel (Microtouch™, Model # RES-6.4-PL4, 3M Inc.). This touch panel was selected because: a) the PL material is non-ferromagnetic and easily attached to shielded and filtered cabling to ensure fMRI-compatibility; b) accuracy and report rate (0.005 inches and a default of 180 reports/sec, respectively) as measured for the functioning prototype exceeded performance criteria, c) use with an MRI-compatible stylus is supported, as well as any form of reasonable touching achieved by movement of a body part; d) the component was readily available with ease of assembly and system integration; and e) the component was affordable (less than $100 US for the touch panel and USB touch screen controller). It is noted that numerous other touch panel technologies are available, such as capacitive or infrared systems, and could be rendered MRI-compatible by employing non-ferromagnetic materials in their construction.

The example touch panel described in U.S. Pat. No. 8,073,526 was mounted into a plastic holder to prevent damage to the sensitive surface. The holder and touch panel attach onto a plastic frame using a series of plastic screws. The position of the plastic holder on the frame can be modified by using a different set of mounting holes located in the frame. The top surface of the frame is attached to two support legs that sit on the sides of the patient table. In certain applications these legs can be firmly affixed to the patient table using a set of specially designed table clamps (not shown).

The top surface of the frame, with the touch panel attached, can be adjusted in various different ways to accommodate the subject who lies underneath. For example, the angle of the example touch panel frame can be changed from 35 degrees to 90 degrees (i.e. perpendicular to the subject's body). In addition, the overall height of the device can be changed from 20 cm to 40 cm above the table surface on which the patient is lying. Limiting these adjustments for writing and drawing are the confines of the magnet bore, which for typical MRI systems range from 55 to 70 cm in diameter.

Figure 2:
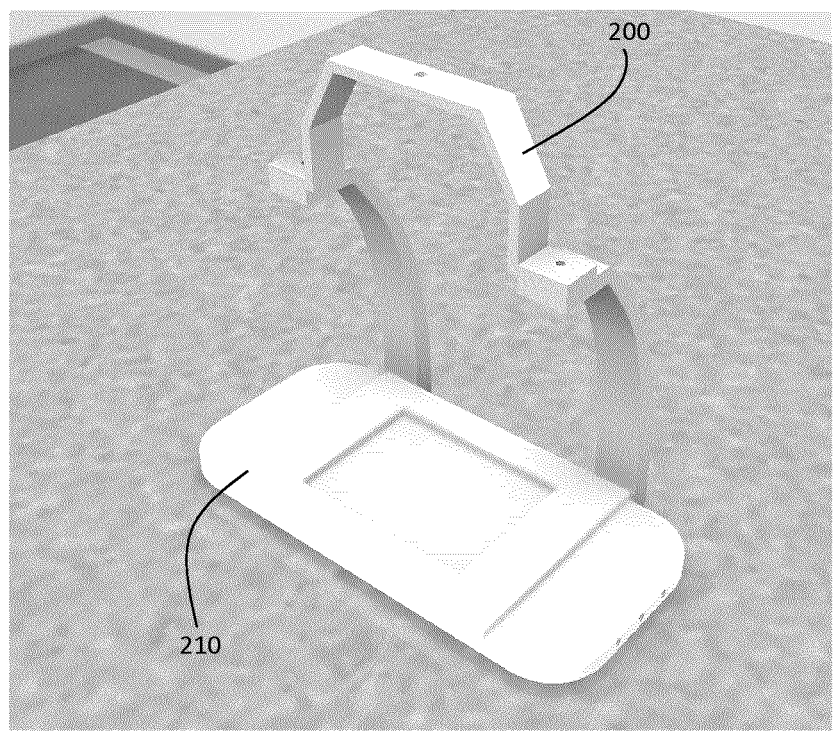
FIG. 2 is an illustration of an example support structure for mounting one or more cameras above a touch panel.

FIG. 2 illustrates an example implementation of a supporting mount 200 for video camera 125. The supporting mount 200 attaches to the plastic frame 210 surrounding the touch panel, in a manner that arches vertically over the center of the touch panel and enables positioning of a video camera (not shown) to acquire video data of hand movements during behavioural performance. Supporting mount 200 is of dimensions consistent with the confines of the magnet bore, and the optical characteristics of the video camera lens to enable high resolution video of the entire touch panel surface and surrounding proximity.

FIG. 1 also illustrates an example implementation of a control and processing unit 110, which includes one or more processors 150 (for example, a CPU/microprocessor), bus 152, memory 154, which may include random access memory (RAM) and/or read only memory (ROM), one or more internal storage devices 156 (e.g. a hard disk drive, compact disk drive or internal flash memory), a power supply 158, one or more communications interfaces 160, display driver 162 for providing a video signal to display 115, a video capture card 180 for capturing and digitizing video from camera 125, touch panel interface 185 for receiving input from touch panel 120, and input/output devices 164. As shown in the figure, signals from two or more of the cables connected to display 115, touch panel 120, and camera 115 may be interfaced onto a common cable through an interface device 130. Non-limiting examples of input/output devices 164 include a speaker, a display, an imaging sensor, such as those used in a digital still camera or digital video camera, a clock, a user input device, such as a keyboard, a keypad, a mouse, a position tracked stylus, a position tracked probe, a foot switch, and/or a microphone for capturing speech commands.

Although only one of each component is illustrated in FIG. 1, any number of each component can be included in the control and processing unit 110. For example, a computer typically contains a number of different data storage media. Furthermore, although bus 152 is depicted as a single connection between all of the components, it will be appreciated that the bus 152 may represent one or more circuits, devices or communication channels which link two or more of the components. For example, in personal computers, bus 152 often includes or is a motherboard.

In one embodiment, control and processing unit 110 may be, or include, a general purpose computer or any other hardware equivalents. Control and processing unit 110 may also be implemented as one or more physical devices that are coupled to processor 150 through one of more communications channels or interfaces. For example, control and processing unit 110 can be implemented using application specific integrated circuits (ASICs). Alternatively, control and processing unit 110 can be implemented as a combination of hardware and software, where the software is loaded into the processor from the memory or over a network connection.

Control and processing unit 110 may be programmed with a set of instructions which when executed in the processor causes the system to perform one or more methods described in the disclosure, such as, but not limited to, image segmentation, extraction and superposition. Control and processing unit 110 may include many more or less components than those shown.

While some embodiments have been described in the context of fully functioning computers and computer systems, those skilled in the art will appreciate that various embodiments are capable of being distributed as a program product in a variety of forms and are capable of being applied regardless of the particular type of machine or computer readable media used to actually effect the distribution.

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like.

Figure 3:
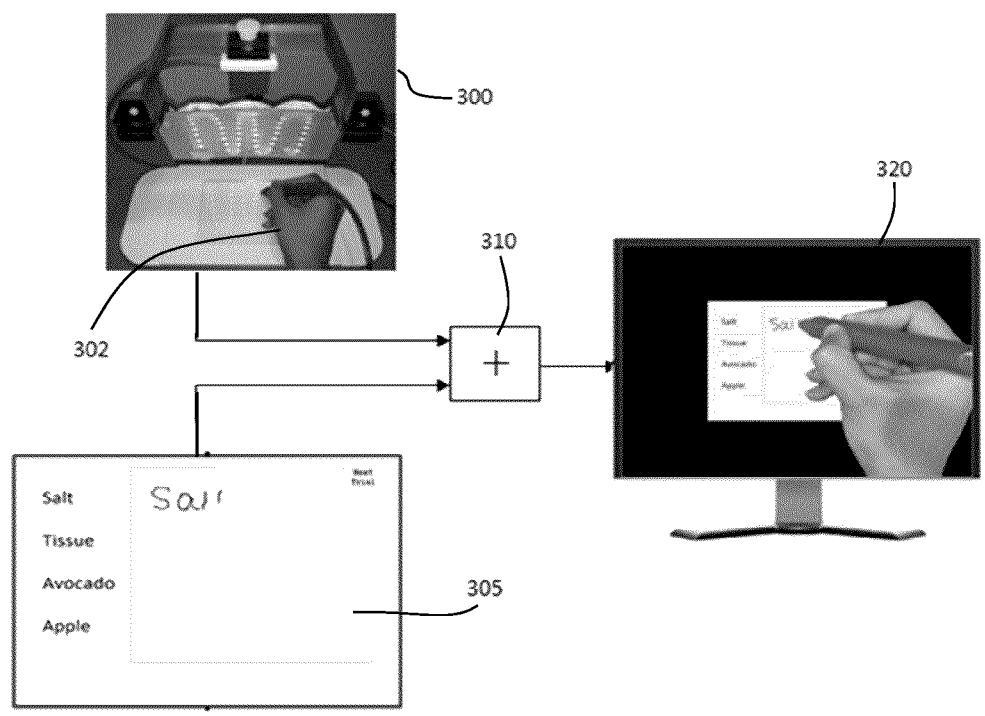
FIG. 3 schematically illustrates the process of superimposing the segmented image of the subject's hands with the input and task related images for display to the subject in real-time.

Referring now to FIG. 3, an illustration is provided that outlines the process of image segmentation and superposition. The video image 300 from the camera is processed to segment the region 302 associated with the subject's hands. A superposition 310 is performed on this image and the input- and/or task-related video images 305, in real time, to produce the composite image 320 that is transmitted to the display. The composite imaging may include an image or representation of at least a portion of the touch panel.

To ensure that the touch panel input is correctly aligned in space with the input- and/or task-related video images 305 as they appear within composite image 320 despite any slight offset of the camera centre from the touch panel centre (with the camera rigidly mounted using a support as shown in FIG. 2 and performing image processing as in FIG. 3), a calibration procedure may be performed before first use. The calibration procedure is normally provided by the touch panel controller vendor and consists of touching several points on the touch panel at locations indicated on the display, and then automatically storing parameters that allow the touch panel driver software to map touch panel locations to display locations. To ensure alignment of touch panel inputs to input/task-related video images 305 in this implementation, one may perform the calibration procedure by touching the indicated locations as they appear in the composite image 320.

It will be understood that the hands of the subject (and optionally a stylus held by the subject) may be segmented according to any one of several known image segmentation methods. In one example embodiment, the hands may be segmented from the recorded images using a skin colour detection algorithm. An example algorithm is the skin colour detection algorithm provided by Solina et al., 2003. Human skin has a special colour distribution that differs significantly from the touch panel colour in the background. In any given colour space, skin colour fills a portion of such space [Kovac et al., 2003].

For example, the Red-Green-Blue (RGB) space may be chosen as the desired colour space. The skin colour segmentation rule based on uniform daylight illumination [Solina et al., 2003] may be utilized to cluster skin coloured pixels. Each pixel in the RGB image that falls within values defined below was clustered as skin, according to the following rules:

$$R>95 \& G>40 \& B>20 \&$$

$$\max\{R,G,B\}-\min\{R,G,B\}>15\&$$

$$|R-G|>15 \& R>G \& R>B.$$

The stylus may be coloured such that its colour falls within the relevant range of values in RGB space, enabling its segmentation and extraction. Image processing operations may then be applied to segment both the hands and the stylus from each camera frame. The extracted and segmented hands and stylus may then be superimposed in a single image frame 320 that can be displayed to the subject in real time.

This skin colour detection algorithm was chosen because of its efficiency and simplicity of operations. Such a simple segmentation algorithm provided real-time capability (it was fast enough to display the segmented hand and stylus appropriately before the next video frame was available).

In another example embodiment, the segmentation algorithm may use the RGB values of the camera video image to select areas of the scene by searching for a predetermined key colour and then displaying the input/task-related video 305 in only those selected areas of composite image 320. The key colour most commonly used in commercial broadcasting for similar overlay masking is a vivid green hue, chosen for its dissimilarity to skin colour and its ease of detection. The key colour may be applied on the touch panel or under it if the panel is transparent. Key colour hue detection may be done most efficiently under good lighting conditions using the original camera image 300 RGB values, by searching for a high green value relative to red and blue, above a predetermined threshold. Alternatively, for key colour detection less susceptible to moderate variations in lighting intensity, the RGB values may be transformed to the Hue-Saturation-Value (HSV) equivalent representation. The key colour can then be found by searching for a Hue value close to the key colour hue, while ignoring very high or very low Saturation or Value which are due to extreme shadows or highlights.

As mentioned above, an initial calibration step may be used to localize the touch panel so that the input/task-related video 305 can be transformed to match the area of the touch panel in composite image 320 despite any slight or moderate offset of the camera centre from the touch panel centre. This calibration is quick and easily automatable, and it also reduces or eliminates the need to redo the calibration procedure described above for aligning the touch panel input to the input/task-related video 305 after moving the camera.

In one example implementation, a calibration procedure may be performed as follows. First, the camera is mounted using a support (for example, as shown in FIG. 2) and a camera image 300 is acquired with the touch panel unobstructed. The area of the touch panel is localized by identifying all the pixels in the image containing a hue similar to the key colour, and determining the maximum extents of the largest contiguous area identified. Subsequently, all input/task-related video images 305 are transformed to fit in the touch panel area and then masked so that only those areas in live camera images 300 that contain the key colour are overlaid with the transformed input/task-related video in the final composite images 320.

In another example embodiment, the touch panel may be a display tablet device that includes an MRI-compatible display screen (e.g. the touch panel may be provided as a touch overlay over a display screen, such as a liquid crystal display [LCD] or light emitting diode [LED] display screen). In such an embodiment, the hands and stylus need not be segmented, and the image recorded by the video camera may be displayed directly to the subject, as it shows both the input and the position and orientation of the subject's hands. It is noted, however, that the previous embodiments involving image segmentation and superposition may provide superior quality rendering for the user, since it potentially avoids problems that may otherwise be encountered in the present direct imaging embodiment, such as glare, poor lighting conditions, shadows, contamination of the tablet surface, and brightness limitations of the display, that may impair the quality of the image that is displayed to the subject.

Although the example embodiments provided herein involve a single camera, it is to be understood that other embodiments may employ multiple cameras to provide an image of the touch panel and the subject's hands. In one embodiment, two or more cameras may be employed to provide a three-dimensional stereotactic display, thereby providing an improved augmented reality experience for the subject.

In one embodiment, the image or rendering of the hand(s) of the subject that is provided in the real-time video may be partially transparent (or partially opaque), such that the portion of the input that is occluded by the subject's hands is visible in the real-time video that is displayed to the subject. This could be beneficial in improving the ability of the subject to provide input, thus potentially increasing the ecological validity of the input.

In some embodiments, a force sensor may be integrated with a stylus, such that a signal associated with the contact force between the stylus and the touch panel is provided. In other embodiments, the touch panel itself may include force sensors, such that it is configured to record the applied force (such as via a pressure sensitive array), such that the input can be provided by an instrument (e.g. a stylus) or directly by finger.

In some embodiments, the force sensor may additionally or instead provide a force-activated binary switch-like input by setting the binary state "off" when force is not applied or is below a threshold, and setting the binary state "on" when force surpasses a threshold. The binary logic can be implemented in hardware or through software with a simple predetermined threshold or a programmable threshold. This force switch function may, for example, be used as a substitute for the previously described stylus microswitch, although in the present embodiment, the force required to activate the switch may be adjustable without replacement of the switch itself. This is useful to accommodate personal preference and people of varying physical abilities. Adjustment may be made, for example, by receiving input from the user via the touch panel specifying a suitable or preferred threshold. In an alternative example implementation, the threshold level may be selected by a selection mechanism (such as a dial or slider) incorporated with the touch panel or the stylus.

In some embodiments, the force sensor responsivity can be adjustable, for example, via adjustment of a gain and/or offset. For example, in one example implementation, the gain and/or offset may be adjusted to such that a threshold force is required to provide input, and this threshold may be based on a typical threshold force employed by a healthy individual to write with a pen or pencil. In another example implementation, the gain and/or offset may be adjusted to provide compensatory adjustments for patients with certain neurological deficits (e.g. stroke) so that they can interact with the tablet more easily.

The processing and control unit 110 may be configured to record one or more signals associated with the input process. For example, the signal provided by the force sensor may be recorded (logged) as a function of time. This provides a record of the time-dependent applied force, which may be processed in order to determine one or more parameters, measures or metrics. For example, the time-dependent recorded force may be processed to determine measures such as the total non-contact time, the total contact time, the percentage of contact vs. non-contact time, and the average applied force when entering input. In other example embodiments, statistical measures associated with handwriting input may be computed based on the time-dependent position of the stylus during contact with the touch panel, such as frequency/spectral measures associated with tremors and other pathological signatures that may be encoded in handwriting and drawing.

As further described below, any one or more of these measures may be employed as behavioural outcome variable during writing and drawing, or biomarkers of pathology, disease, disorders, and/or conditions, or risks thereof. A biomarker may be associated with any one or more measures associated with the time-dependent force, optionally combined with other biomarkers, such as other neurological markers.

In another embodiment, the time-dependent force data may be used as a "covariate of interest" in modelling approaches to map the brain activity from fMRI data. As an example, the most commonly employed method for mapping brain activity is the General Linear Model (GLM). The GLM method assesses at each voxel within functional MR images the degree to which the fMRI signal can be fit to a model waveform (the covariate of interest) of the hypothesized neural activity mathematically convolved with a hemodynamic response function that accounts for the sluggish temporal evolution of the fMRI signal over tens of seconds after a brief (~1-1000 ms) neural stimulus. Often the covariate of interest is taken as the task design; however, an alternative approach involves the use of time-dependent behavioural responses. Force data recorded from the tip of the stylus could thus be input to the GLM to map brain activity tightly coupled to writing and drawing responses. This approach is advantageous because it intrinsically controls for response time effects that are not represented when the covariate of interest is taken as the task design (e.g. the timing with which visual cues are presented). The effect is likely to be of most importance when behavioural responses are brief, such as when pointing to targets on the tablet surface.

It will be understood that in some example implementations, the touch panel may additionally or alternatively be compatible with one or more other analysis procedures that can be employed for mapping brain activity from fMRI data, including, but not limited to, procedures based on independent component analysis, partial least squares analysis, canonical variates analysis, and machine learning approaches.

In some embodiments, the visual feedback (and optional pressure sensitive feedback from the stylus described below) is processed and presented to the subject with a time lag that is sufficiently brief such that the subject does not perceive a delay, such that the visual feedback is displayed in real-time. For example, in some embodiments, the acceptable time lag may less than 50 ms, less than 40 ms, or less than 30 ms. This may provide the visual feedback such that it will not be detectable as an error signal with the brain in relation to the sense of proprioception (i.e. the bodies awareness of limbs in space to two sensors and tendons and muscles). Accordingly, in such an embodiment, the processor and related components are capable of rapid recording and fast image processing. The inventors have found that using the components described in Examples 1-3 below, the system was sufficiently real-time in nature that no observable effects of sensory conflict were apparent. Specifically, the visual feedback of hand position was provided with sufficiently minimal lag to avoid introducing lag between visual information and proprioceptive sense of limb position. Such an affect would have strongly impacted the ability to demonstrate improved behavioural performance when using the tablet with visual hand feedback.

Although example values of acceptable time lag maximal values have been provided above, an empirical or experimental protocol may be employed to determine or otherwise measure a suitable maximal time lag for achieving a perception of real-time rendering of the video that is provided to the subject. In one example implementation, a subject may be asked to perform one or more tasks in a serial fashion, where the time lag associated with the rendering of the video is varied each time the task is performed. The time lag, when perceived by the subject, will result in an associated pattern, effect or signature that is visible in or obtainable from the fMRI data, due to a degradation in performance with increasing time lag. The performance will be impaired when the time lag exceeds the threshold where sensory conflict comes in to play. Impairments that are likely include lengthened time to respond, reduced spatial accuracy, and atypical contact forces. Thus, the measured impairment, and diagnostic capability described below, can come both from the fMRI data and the tablet behavioural recordings. In other words, by manipulating the time delay and extending it, there is sensory conflict between visual feedback of hand position (which is delayed) and the sense of proprioception (which is real-time), which will be evident in the recorded fMRI image data and possibly also the input recorded via the tablet. When the time delay is lowered below the threshold associated with the perception of real-time video, the fMRI patterns and tablet input may become substantially time invariant. Therefore, by monitoring the fMRI images and/or tablet input, as a function of time lag, one can identify a value for the maximal time delay that is appropriate.

This method may be performed on a single subject, in order to obtain a per-subject, or "personalized", value of the maximal time lag, or it can be performed across a population of subjects to identify a statistically derived maximal time lag. In one example, a statistically derived maximal time lag may be obtained based on a sub-segment of the population. For example, if the subject is a healthy subject without a known impairment or diagnosis, the maximal time lag employed when performing fMRI studies and rendering video according to the methods described herein may be obtained as the maximal time lag that is statistically derived from a population of healthy subjects. Similarly, if the subject has a diagnosed medical condition, such as Alzheimer's disease, the maximal time lag employed when performing fMRI studies and rendering video according to the methods described herein may be obtained as the maximal time lag that is statistically derived from a population of subjects sharing the medical condition.

In one embodiment, the preceding method may be employed to determine, on a per-subject basis, the threshold time lag below which the perception of the time delay is no longer evident as per the fMRI image data and/or table input data. This measured threshold time delay may be employed as a diagnostic marker, or, for example, as an input to a multiplexed marker derived from a plurality of diagnostic measurements. Lag appreciated by the brain will hinder behavioural performance and will force certain brain areas, such as the anterior cingulate, to activate as part of conflict resolution and error processes. This could be diagnostic for certain patients (AD, stroke, traumatic brain injury, even normal aging) and could be used to determine threshold for sensory conflict. In the pathological processes indicated, speed of information processing can be a symptom and this would be a process for quantifying it/detecting it in relation to the normal population.

For example, if representative threshold time lag data has been measured on a per-population basis for a number of different medical conditions or disease states, it may be possible to compare the measured threshold time lag for the given subject to the threshold time lag data for the various medical conditions or disease states in order to provide a biomarker suitable for diagnosis, and optionally, to perform the diagnosis.

In some embodiments, the visual display that is provided to the subject is rendered such that the displayed input is dependent on the force measured by the force sensor. For example, the thickness of a line drawn by the user (for example, when drawing or writing), may be rendered according to the applied force, such that when the subject presses harder on the touch panel, thicker lines are shown, while when the subject presses more lightly, thinner lines are produced. Such a rendering method is consistent with the process of writing using a pencil or pen in a real world setting, and therefore provides the subject with an experience that is more likely to provide ecologically valid input such that the fMRI data are more strongly correlated with the task itself than with confounds associated with the tablet interaction. This embodiment also provides a visual feedback that is more consistent with the tactile feedback involving the interaction of the writing instrument (or finger) with the touch panel.

In another example implementation, the time duration during which a pixel associated with contact between the touch panel and the subject (e.g. via direct finger contact or via a stylus) is displayed may depend on the force or pressure that was locally applied. This may also provide for feedback that enhances the ecological validity of the data that is obtained.

In another example embodiment, the stylus may be rendered in the visual display in a form that differs from the physical geometry of the stylus, in order to improve the user experience and the perceived accuracy of positioning the tip of the stylus. For example, the stylus may physically have a blunt tip, but may nonetheless be rendered as having a sharper tip. This may provide the subject with improved confidence in positioning the stylus based on the visual feedback, and may thus contribute to providing input that is more ecologically valid. In another example, the stylus may be rendered to resemble a conventional writing instrument, such as a pen or a pencil.

Embodiments in which the input can be provided across a wide range of applied forces, with the input being rendered in a manner that is dependent on the applied force, may overcome another drawback associated with the aforementioned crosshair/microswitch input method. It has been found that individuals providing input according to the crosshair/microswitch input method often have a tendency to overcompensate and press harder than is needed to activate the microswitch. This causes difficulties in determining the appropriate force for triggering the microswitch, and can lead to a frustrating, time-consuming, inefficient, and inaccurate trial and error process in which the subject attempts to determine the appropriate pressure for consistent writing and drawing.

It is to be understood that the preceding embodiment is but one example method through which the rendering of the input on the visual display is dependent on the interaction between the stylus and the touch panel. In another example embodiment, the orientation of the stylus relative to the touch panel may be determined (e.g. via one or more sensors such as gyroscopic sensors, accelerometers, and/or fiducial markers that are detectable by a navigation system), and the thickness of a rendered line during contact may be dependent on the angle of the stylus, thus mimicking the real-world behaviour of a pencil or pen having a tip with a finite extension. For example, if the stylus is determined to be angled relative to the touch panel in a near-orthogonal orientation, the rendered line during contact may be thinner than the line that would have been rendered had the stylus been rendered at an oblique angle.

In one example implementation, a glove may be work on one or more hands of the subject in order to facilitate the image segmentation process. For example, a glove having a uniform color may be employed, such that the image of the user's hand can be segmented as per the methods described above. Such an embodiment may facilitate image segmentation of the subject hand or hands even when there is considerable variation in skin colour and pigmentation among different subjects, or, for example within the hand of a single subject. In other example implementations, the glove may include one or more fiducial markers that may be employed for, or to support, image segmentation. For example, passive fiducials or glyphs may be used, or active light emitting fiducials may be used, provided that they are compatible with use within an MR scanner. A plurality of fiducials may be used in some embodiments, for example, for marking the tips of individual fingers and thumbs, or other anatomical landmarks such as knuckles.

It will also be understood that although many of the examples provided in the present disclosure pertain to the use of the recording of images of the hand or hands of the subject for image segmentation, the imaging technology employed for this purpose need not be a two-dimensional imaging technology, and may instead employ three-dimensional imaging and/or surface profilometry/topology determination for subsequent segmentation and rendering of the hand or hands of the subject. Such embodiments may be useful in allowing the viewpoint that is rendered to the user to be different from the viewpoint that is recorded by the imaging device. Examples of imaging devices and modalities that may be employed for such embodiments include, but are not limited to, stereoscopic imaging, structured light imaging, modulated light, laser radar, and three-dimensional laser scanning.

In yet another example embodiment, the thickness of a rendered line or point may be dependent on the translational speed of the stylus during contact with the touch panel. For example, a relatively thinner line may be rendered when the stylus is contacting the touch panel and moving at a fast speed, while a relatively thicker line may be rendered when the stylus is contacting the touch panel and moving at a slow speed. Furthermore, if the stylus is held at rest and in contact with the touch panel under an applied force, the radius of the rendered point may increase with time. These example embodiments provide a visual rendering of input that is associated with the real-world behaviour of some types of pens.

It will be understood that any or all of the aforementioned methods of controlling the rendering of the input based on the interaction between the stylus (or finger) and the touch panel may be combined, such that the rendered graphic is dependent on parameters such as applied force, stylus orientation, and or relative speed.

A number of embodiments are foreseen that relate to therapeutic and diagnostic applications of the disclosure. Considering therapeutic applications first, the ability to quantify writing, drawing, and touch responses in an ecologically valid manner while interacting with the touch panel may provide benefit for neurosurgical pre-operative planning. In such applications, the target volume (e.g. tumour or epileptogenic focus to be treated, or deep brain nucleus targeted for deep brain stimulation) can be localized and depicted using various MRI protocols, including anatomical MRI, MR spectroscopy, MR perfusion imaging, diffusion-weighted imaging, and simultaneous use of fMRI and electroencephalography (EEG).

In some clinical scenarios, it may potentially be necessary to monitor behavior to show that a behavioral deficit has been alleviated directly by the therapy, or to ensure that baseline behavior is not otherwise altered by the treatment (no side effects are introduced to behavior). The present systems and methods can be employed for this purpose (See, for example, Example 4).

For example, in MR guided focused ultrasound treatment of essential tremor, of the treatment procedure is to target the thalamic region of the brain in order to suppress uncontrolled movements of the hand that significantly impact quality of life. Current behavioral assessment during therapy is remarkably crude, consisting of the neurologist or neurosurgeon having the patient attempt to point and touch to the hand of the clinician while the subject is in the magnet bore. There are a variety of paper and pencil assessments for essential tremor; the use of the touch panel with visual feedback during essential tremor treatment in the MRI system would enable a far more quantitative and subtle assessment of tremor behavior and subsequent suppression during therapy. It could enable more precise targeting of the brain region of interest that needs to be ablated, as it is possible with the high intensity focused ultrasound to deliver thermal those just below the threshold of ablation prior to administering the full dose. The approach would enable the treatment plan to be delivered more rapidly and effectively and perhaps more completely. Post-treatment essential tremor tablet performance could be quantitatively evaluated by behavioral measures that would consist of deviations from prescribed drawing behavior (e.g. a straight line and a spiral) as well as Fourier transform analysis of drawing behavior to show the attenuation of the tremor frequency over the treatment.

In one embodiment, the apparatus and methods described herein, through administration of various neuropsychological tests in combination with fMRI, enables the mapping of "eloquent" areas of the brain. These areas are responsible for processing sensations, movement, and language; if damaged during therapeutic procedures, the consequence can be significant, permanent, behavioral side-effects that affect the patient's subsequent ability to return to the work force, or reduce the patient's quality of life. Thus, the task of the neurosurgeon may involve removal abnormal brain tissue while minimizing damage to eloquent areas. The use of the tablet with visual feedback of hand position has applicability in this context, providing improved maps of ecologically-valid brain activity prior to surgery, to assist in neurosurgical planning. However, the concept of mapping eloquent cortex in this manner also is applicable to MRI-guided neuro-interventions that are non-invasive (e.g. using high intensity focused ultrasound) or minimally invasive (e.g. local drug delivery or use of cryoprobes, laser probes, or radiofrequency probes for thermal therapy).

The touch panel could also be used in neurosurgical planning applications prior to surgery. For example, it is critically important for neurosurgeons to establish fine motor skill and language areas within the brain and functional MRI is receiving increased attention for its ability to provide non-invasive activation maps in conjunction with other presurgical planning information such as diffusion tensor imaging, magnetic resonance spectroscopy, anatomical MRI, perfusion MRI. In the case of language mapping, there are established behavioral tasks for mapping language areas but these provide reduced sensitivity and specificity compared to the mapping of motor regions. Part of the reason for this is that the conventional tasks that are utilized do not completely encompass all ecologically of valid language functions. Language tasks that are implemented on the tablet that include writing and drawing can provide an additional window on language areas that helps to improve the sensitivity and specificity of the resultant activation maps.

For example, "eloquent" maps, which provide essential information for a neurosurgeon to formulate a plan to treat the lesion volume while sparing as much of the eloquent regions as possible, could be employed to minimize the possibility of surgical side effects. Possible example applications include using interactions with the touch panel to map the brain regions responsible for fine motor skills (e.g. primary motor cortex, supplementary motor area, pre-motor area, insula, basal ganglia, cerebellum), reaching and grasping (e.g. intra-parietal sulcus), language (e.g. Broca's and Wernicke's areas), memory (e.g. hippocampus and parahippocampus, prefrontal cortex), attention (e.g. dorsolateral pre-frontal cortex), executive function (e.g. pre-frontal cortex), and processing of emotions (e.g. orbito-frontal cortex).

A related example embodiment relates to mapping these eloquent areas by fMRI conducted during MR-guided therapeutic interventions to provide real-time evaluation, where input from the subject is provided by interaction with the touch panel. This may be beneficial during invasive procedures where the brain parenchyma shifts spatially due to the creation of burr holes or craniotomies, as required to perform surgical procedures and/or insert therapeutic devices into the brain. In such cases, fMRI results acquired pre-operatively will be spatially inaccurate.

In other embodiments, the systems and methods disclosed herein may be employed for post-intervention or post-treatment monitoring. For example, in the days, weeks, and months post-therapy, the systems and methods disclosed herein may be employed to monitor treatment response, check for remission, or assess the need for alternative therapies.

The systems and methods disclosed herein may also find applications in research methodologies, such as neuroscience and neurosurgical research.

The systems and methods disclosed above may also be employed for disease diagnosis via fMRI. Examples include the use of combined touch panel-based neuropsychological tests and related fMRI maps of brain activity as a biomarker for early detection of neurodegenerative disease (e.g. Alzheimer's disease). In such a scenario, it may be possible to detect behavioural and related brain activity impairments well in advance of neuron loss due to atrophy, with the opportunity to intervene at this time with protective or even curative therapies to prolong quality of life. Another example involves patients that have survived the acute phase of stroke, for which assessments of behaviour and brain activity with the systems and methods disclosed herein may enable selection of the specific form of rehabilitation therapy (physical, cognitive, or occupational) specially tailored to treat the needs of the individual patient, and potentially even improve prognosis for recovery. Such capabilities are sorely needed given the heterogeneity of brain impairments and recovery potential characteristic of stroke patients.

In another example implementation, the systems and methods described above may be employed for the assessment of patients with mild traumatic brain injury, enabling improved assessment of injury severity and selection of appropriately tailored interventions. This area is receiving increased attention given the heightened awareness of the potentially devastating long-term consequences of one or multiple concussions in professional athletes.

The following examples are presented to enable those skilled in the art to understand and to practice embodiments of the present disclosure. They should not be considered as a limitation on the scope of the disclosure, but merely as being illustrative and representative thereof.

EXAMPLES

Example 1

Experimental Study of Effect of Visual Feedback on Writing Performance without fMRI To test the effectiveness of visual feedback of the subject's hand position, nine young healthy adults performed handwriting tasks in front of a computer display with two different modes of usage: with and without visual feedback of hand movements (subsequently referred to as "visual hand feedback"). Based on the arguments given above, it was hypothesized that behavioural performance would improve when comparing use of the touch panel with and without visual hand feedback.

Nine young healthy adults (age 20-35; 4 male, 5 female), right-handed and free from previous or existing neurological and psychiatric impairments were recruited from student pools at the University of Toronto. The study was approved by the Research Ethics Board at the Sunnybrook Health Sciences Centre.

The MRI-compatible touch panel used in these experiments included a touch-sensitive surface (13 cm×10 cm) that converts localized contact force to position coordinate values, which can then be interpreted and translated to an effect at the corresponding point on the computer display [Tam et al., 2011]. The stylus included a force sensor capable of measuring the value of the applied force. The spatial resolution of touch was 0.13 mm and the report rate was 180 Hz.

The touch panel was interfaced with a stimulus/response computer running a custom program written using E-Prime software (version 2; Psychology Software Tools, Inc., USA) that received the touch position information, processed and interpreted the information, and generated an input/task-related video signal for display to the subject. The video signal included task-related instructions and images (such as words to be copied, shapes to be traced or copied, or boxes to check), an indication of the cursor position, and visual representations of the input provided by the subject.

To enhance task-related feedback from the touch panel, an MRI-compatible video camera (MRC Instruments, Germany) was mounted over the touch panel to capture streaming video of hand motion during task performance at 30 Hz. The field of view of the camera was the entire touch panel surface and a portion of its surrounding supporting frame. The camera was mounted to the support structure of the touch panel via an overhead mounting frame.

The aforementioned skin colour detection algorithm was used to determine pixels that include skin [Solina et al., 2003]. In the present study, Red-Green-Blue (RGB) values were chosen as the desired colour space. The skin colour segmentation rule based on uniform daylight illumination [Solina et al., 2003] was used as the starting point to cluster skin coloured pixels, with slight adjustment of the R and G threshold values to increase effectiveness of the algorithm in the fMRI environment and in our laboratory environment outside the magnet. Each pixel in the RGB image that fell within values defined below was clustered as skin:

$R>55\&G>20\&B>20\&$ $\max\{R,G,B\}-\min\{R,G,B\}>15\&$ $|R-G|>15\&R>G\&R>B.$

In addition, the stylus was covered by a red membrane, the values of which fit within the above range of values in RGB space. This ensured that both the stylus and the hand were segmented from each video frame.

Images from both the E-Prime-based stimulus/response computer and the MRI-compatible video camera were captured via two video capture cards (ImpactVCB-e; Hauppauge Computer Works, USA) on a second computer running a custom program written in Matlab (The Mathworks, Inc., USA). The image processing operations described above were implemented in this program to segment and extract the images of the hand and stylus from each camera frame.

The extracted images of the subject's hand and the stylus were also superimposed on the E-Prime video signal from the stimulus/response computer, such that the images displayed to the subject included real-time rendering of the visual stimuli, tablet responses, and also real-time rendering of the subject's hand and the stylus. The rendered video signal was provided at a frame rate of 30 Hz. As The threshold time tag described above, associated with a perception of a lack of real-time video, was found according to the present experimental examples for be greater than the time associate with a video frame, i.e. $\frac{1}{30}$ Hz=33 ms. It is expected that the time between sensory stimulus and activation of primary sensory cortex is approximately equal to, or greater than, this value. No behavioural perception of lag was observed by subjects in any of Examples 1-3.

Three writing tasks commonly used in everyday activities were modified for use during fMRI writing tasks, following the approach of Werner et al. (2006). The tasks involved copying a grocery list, copying phone numbers, and copying a paragraph. In each trial, a list containing four grocery items, or two phone numbers appeared on the left side of the screen, with a box located on the right side next to the list for handwriting, as shown in FIG. 3 at 305. For the paragraph task, subjects were required to write in a box located below the paragraph.

Each task was repeated four times, or "trials". Two different tablet usage modes were investigated: with visual feedback of hand position (with VFHP) and without visual feedback (without VFHP). Tasks and usage mode were randomized across subjects to avoid sources of systematic bias (such as motor learning effects). Each trial of the paragraph task contained the same number of words, with sentence re-arranged while maintaining correct English grammar. This procedure was intended to encourage subjects to focus attention on the copying task consistently throughout and to avoid copying large sections of the text by memory. Subjects received training on using the touch panel prior to performing handwriting tasks. Subjects were instructed to be as accurate and quick as they could, and not to look at their hands placed on the touch panel during the entire experiment (note that this initial experiment was performed outside of an MRI bore). Subjects were then instructed to use the touch panel and stylus to copy the items required in each task . . . . Each collection of four words, or two phone numbers or a paragraph constituted a single trial. At the end of each trial, the subject advanced to the next trial by pressing within a small box (described as a "tab") labelled "Next Trial" at the top right of the touch panel.

During writing tasks, the following measures were recorded and calculated using the touch panel, stylus and E-prime software, for every trial including copying grocery and phone number lists and copying a paragraph: 1) mean stylus pressure applied by the subject against the touch panel; and 2) completion time for each trial. Pressure was sampled every 25 ms. In addition, the time that the stylus was held in the air during the tasks was also determined by calculating the difference between task completion time and the time that the stylus was in contact with the touch panel. Results of Example 1 are provided in FIGS. 4 to 5.

Figure 4A:
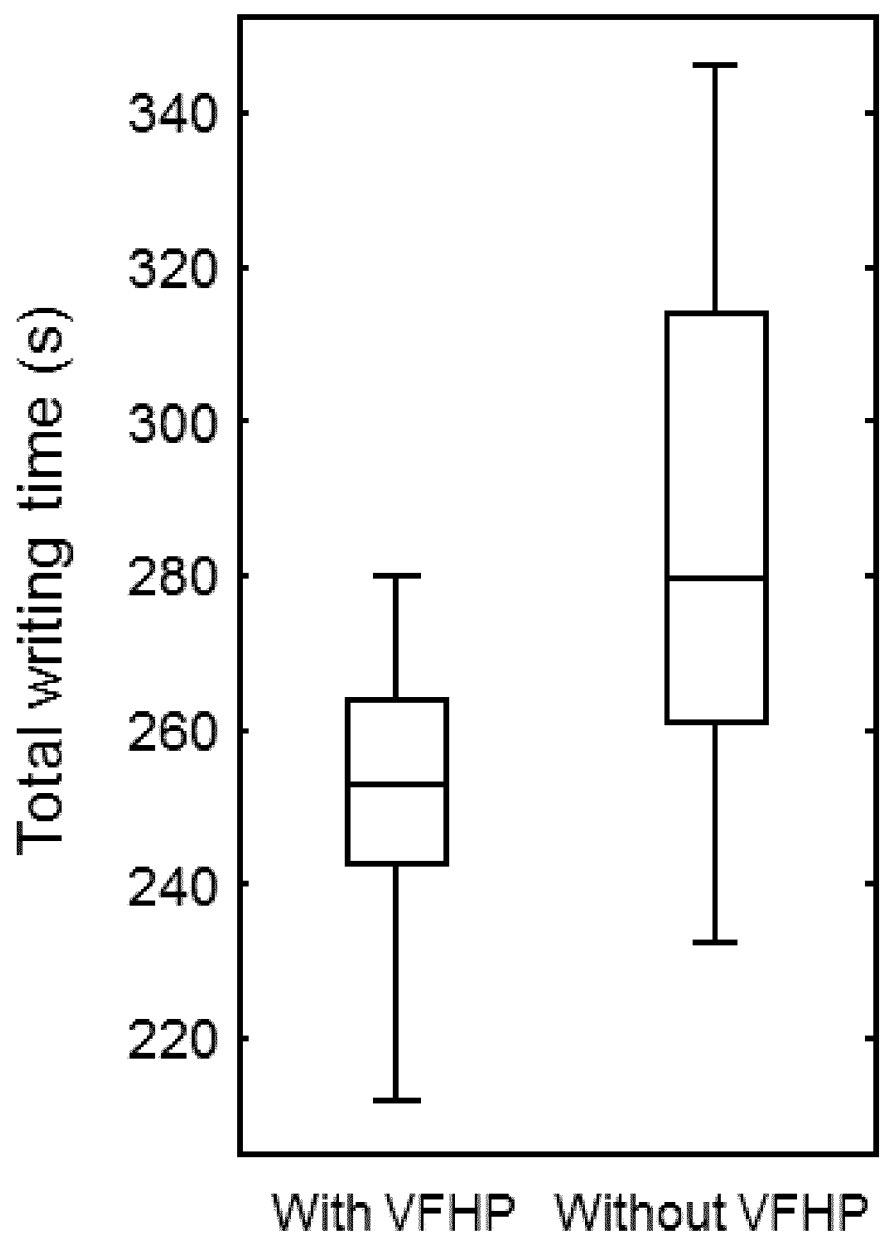
FIG. 4A shows the total time for completing copying tasks (copying a grocery list, copying phone numbers) in nine young healthy subjects with and without visual feedback of hand position (VFHP).
Figure 4B:
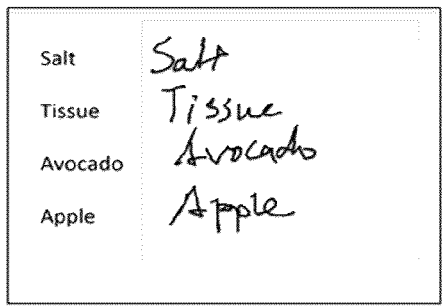
FIG. 4B shows representative screen-shot results of writing performance from a single young healthy subject copying a grocery list, with and without VFHP.
Figure 4B:
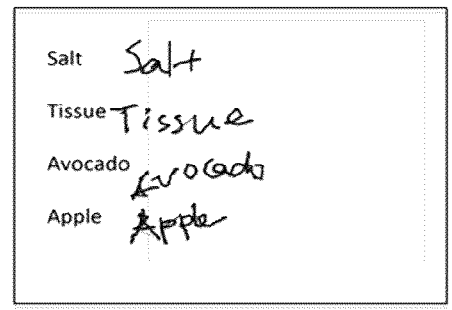

FIG. 4A shows a box and whisker plot of the mean total completion time for the nine subjects when performing all trials of the phone number and grocery list copying tasks with VFHP and without VFHP. Subjects required significantly less completion time with VFHP than without VFHP ($p<0.05$, Wilcoxon signed-rank test). Behavioural performance for one subject performing the grocery list task is shown in FIG. 4B. With VFHP, the writing is slightly neater and placed well within the response box, compared to performance without VFHP, during which the subject had difficulty initiating tablet responses in the correct location with writing slightly outside the left edge of the box. This difficulty in locating the cursor position was also observed when subjects had to press the "next trial" tab in the without VFHP (data not shown), contributing to the longer completion time in relation to performance with VFHP.

Figure 4C:
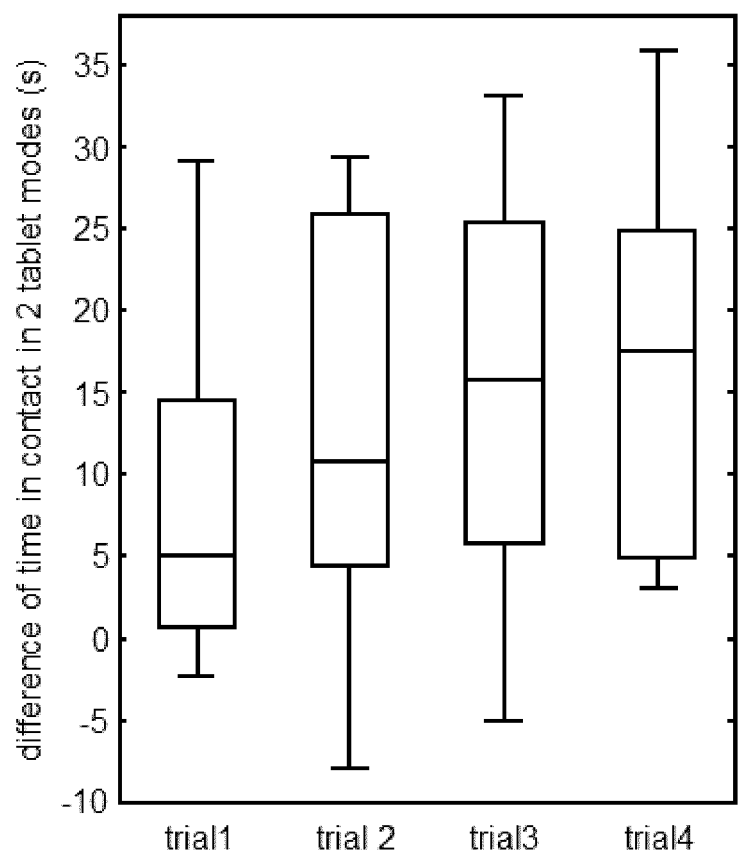
FIG. 4C shows the difference in total time that the stylus was in contact with the touch sensitive surface of the tablet, for young healthy subjects copying paragraphs (without VFHP minus with VFHP), across four trials.

FIG. 4C shows the difference in time that the stylus was in contact with the tablet during copying of paragraphs (without VFHP minus with VFHP). There was a statistically significant main effect of trial number on time difference, as determined by a 2-way repeated measured analysis of variance (ANOVA) with tablet mode (with, without VFHP) as the fixed factor and subjects as the random factor ($p<0.01$). In the first trial the time difference between use of the two tablet modes was relatively small (approximately 5 s). Subsequently, the difference plateaued to approximately 15 s by trial 3 and increased little thereafter. Subjects kept the stylus in contact with the tablet for longer when performing without VFHP because in this condition they placed more reliance on the cursor to locate where to write in space. When performing with VFHP, they were able to write more naturally based on receiving visual input of the position of their hand, and the tip of the stylus.

Figure 5A:
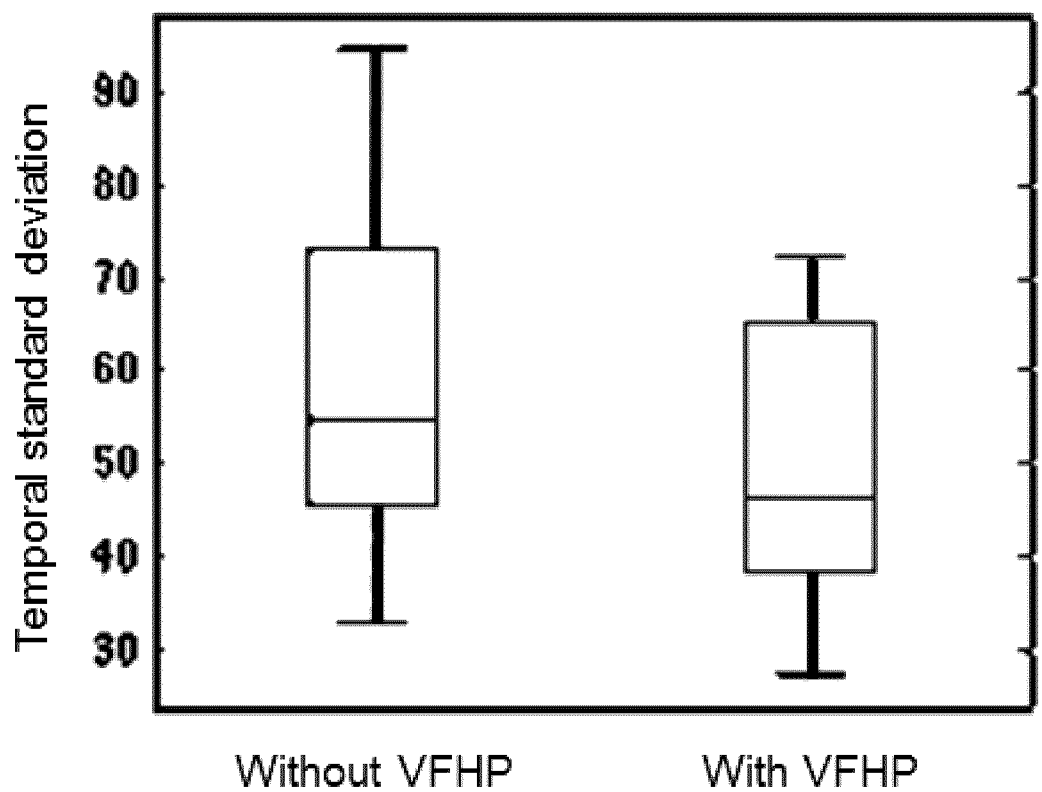
FIG. 5A shows the temporal standard deviation of force recordings from the stylus tip for young healthy subjects copying paragraphs using the tablet without VFHP, and with VFHP.
Figure 5B:
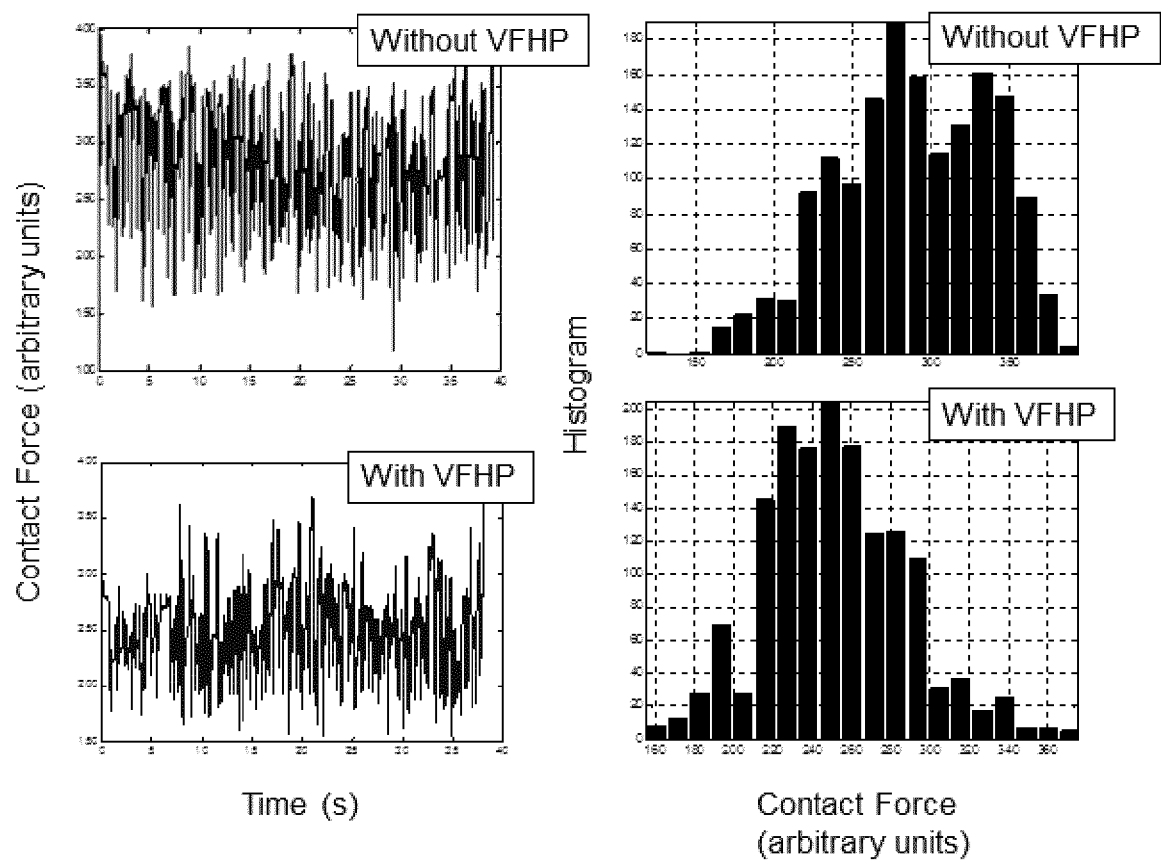
FIG. 5B shows forces recordings and associated force histogram data for a representative young healthy subject copying paragraphs using the tablet without VFHP and with VFHP.

FIG. 5A shows a box and whisker plot of the temporal standard deviation of force as subjects made contact with the tablet to copy paragraphs with or without VFHP. On average, the standard deviation was larger without VFHP and showed more variability (Wilcoxon signed rank test, $p<0.05$). FIG. 5B shows force examples for a single representative subject. The subject used more contact force with the stylus over time when using the tablet to copy paragraphs without VFHP (FIG. 5B top left), versus use with VFHP (FIG. 5B bottom left). The associated force histograms are shown in FIG. 5B top right, and FIG. 5B bottom right, respectively, with the latter showing a shift to lower force values. It should be noted that the axis ranges on each of the plots shown in FIG. 5B are different. Less contact force when using the tablet with VFHP compared to without VFHP is consistent with subjects experiencing a more intuitive stylus-tablet interaction.

Overall, . . . the results shown in FIGS. 4A-C and FIGS. 5A-B are consistent with the hypothesis that providing the user with visual feedback of hand motion while interacting with the touch panel leads to improved and more ecologically valid writing and drawing performance in healthy subjects, that . . . is less demanding of sensorimotor brain regions.

The performance gains that have been documented by this work in healthy young adults have important implication for applying the invention to acquire behavioural and brain activity data in patients. In patients with impaired brain function, the reduction in task difficulty afforded by visual hand feedback will enable them to perform neuropsychological or other clinical tests sufficiently well to probe the intended aspects of brain function, without substantial confounds introduced by the need to perform a challenging sensorimotor task concurrently. For example, in patients with traumatic brain injury or a neurodegenerative disease such as Alzheimer's Disease, decreased ability to divide attention between multiple tasks, or generalized reduction in the speed of mental processing strongly argue for making the task of interacting with the tablet as naturalistic and ecologically valid as possible. In Alzheimer's Disease and in patients suffering from stroke, there is also the possibility of impairment of specific brain regions involved in sensorimotor control that specifically affect writing and drawing ability. In these cases, visualization of hand position is critical to facilitate the recording of significantly impaired movements.

In addition, recording pressure at the tip of the stylus, as demonstrated, enables novel methods to quantify writing and drawing performance. Although performance can be quantified by logging the spatial coordinates of the stylus tip as a function of time, pressure (or equivalently, force) data provide useful supplementary or alternative measures. For example, it is possible to conceive scenarios in which writing and drawing performance is apparently normal based on spatial measures, but is abnormal based on pressure data. Given that the contact force of the stylus on the tablet surface is a function of muscle fibres recruited, a corresponding modulation in the underlying neural activity is also expected. Thus, the recording of stylus pressure provides an additional means of interpreting the maps of brain activity that are generated when using the touch panel with visual hand feedback in fMRI examinations.

Example 2

Experimental Study of Effect of Visual Feedback on Writing Performance with fMRI After having performed the aforementioned initial experiments, an additional set of experiments were performed with the touch panel and a single representative young healthy subject within an MRI scanner for fMRI of writing tasks. These experiments were carried out to map brain activity associated with two different modes of the touch panel for performance of copying paragraphs. The tasks were the same as those described in the preceding example, with the exception that the fixation duration between trials, consisting of a white screen with a central black fixation cross, lasted 16 s for the fMRI experiments.

The experimental setup was similar to that shown in FIG. 1 and employed the components described in the preceding example. The touch panel was placed on a supporting platform to simulate writing on a desk and to accommodate the subject's comfort. The touch panel's platform also kept the writing surface away from the torso to prevent respiratory motion from affecting behavioural performance.

As in the preceding example, the skin colour detection algorithm was employed to extract images of the subject's hand and the stylus. The extracted images of the subject's hand and the stylus were superimposed on the video signal, such that the images displayed to the subject included real-time rendering of the input and the task-related stimuli, and also real-time rendering of the subject's hand and the stylus. The video signal was displayed to the subject on a projection screen via an MRI-compatible projection system (Avotec Inc.). The projection screen was located behind the subject's head, and the subject was able to see visual feedback of the tasks through a mirror placed on the head coil.

All imaging was conducted at 3.0 Tesla using a standard 8-channel head coil (MR750 system, GE Healthcare). Anatomical MRI was undertaken using a standard T1-weighted acquisition method [Macintosh et al., 2008]. Functional MRI was conducted using the spiral in/out k-space trajectory technique [Glover et al., 2001]. All fMRI data were collected with repetition time (TR) 2 s, echo time (TE) 30 ms, flip angle 70°, field of view (FOV) 20×20 cm, number of slices=30, slice thickness=4.5 mm.

Analysis of fMRI data was carried out in "Analysis of Functional Neuroimaging" (AFNI) software [Cox et al., 1996]. Rigid-body motion correction software was used (AFNI 3Dvolreg) to spatially align series of acquired images to a reference image [Cox et al., 1996]. Cardiac and respiratory signals were measured using a pulse oximeter and a respiratory belt strapped around the subject's torso. The physiological noise was regressed from the fMRI data using the RETROICOR algorithm [Glover et al., 2000]. This step was followed by slice timing correction, whereby slices of the same brain volume were aligned to a reference slice in the volume to account for the slight differences in acquisition times between image slices. Spatial smoothing was then applied using a 6 mm full width half maximum (FWHM) Gaussian filter to increase signal to noise ratio (SNR) [Friston et al., 1995]. A GLM analysis subsequently was used to quantify activity within voxels with BOLD signal time-courses that co-vary with the handwriting tasks, in the form of statistical parametric maps (SPMs). After GLM analysis, SPMs was created by performing a significance test, such as a T-test, at each voxel. The maps were thresholded using a False Discovery Rate method [Genovese et al., 2002]. The anatomical image was then aligned with a T1 atlas in Talairach space. Finally, the maps were overlaid on anatomical image.

Figures 6A, 6B:
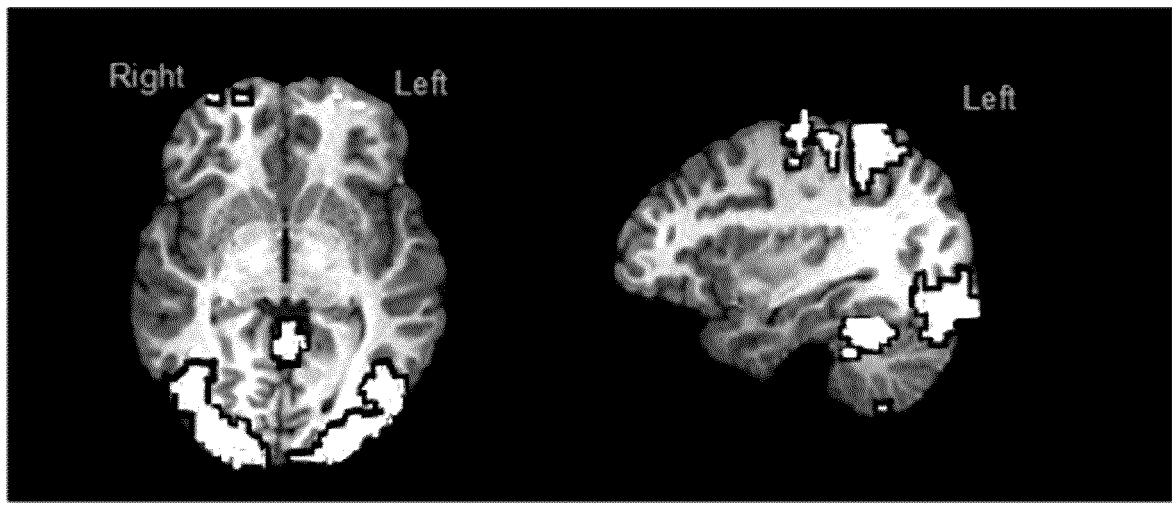
FIGS. 6A-D show measured activation maps for a single young healthy adult copying telephone numbers compared to a rest condition, with (FIGS. 6A and 6B) and without (FIGS. 6C and 6D) VFHP.
Figures 6C, 6D:
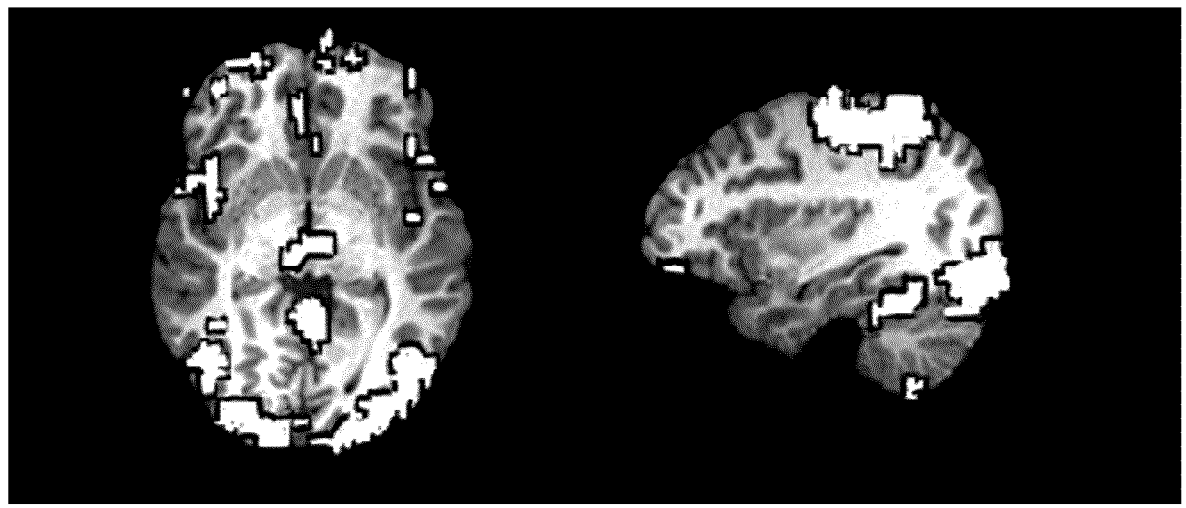

FIGS. 6A-D show the resulting fMRI maps of brain activity for the copying paragraph task with VFHP (FIGS. 6A and 6B) and without VFHP (FIGS. 6C and 6D). Representative grayscale axial images are shown in FIGS. 6(*a*) and 6(*c*), whereas sagittal images are shown in FIGS. 6B and 6D. Coarsely pixelated areas are shown throughout in white overlay to indicate activation areas. For the case of with VFHP, the extent of brain activity is limited to a quite small set of focal regions, whereas without VFHP, extensive areas of brain activity are observed at the same statistical threshold. In other words, with VFHP, the regional extent of brain activity decreased, particularly in cortical sensorimotor areas and frontal areas in comparison to experiments performed without VFHP, suggesting that the feedback promotes use of less neural resources to control improved writing and drawing behaviour.

Example 3

Experimental Study of Effect of Visual Feedback of Hand Position on a Computerized Memory Task Alzheimer's disease (AD) is a major global health burden for which drug development urgently requires improved methods for early disease detection in individual patients. A variety of NP test batteries are used clinically when AD or other forms of dementia are suspected, probing general cognition and mental health, as well as specific cognitive domains such as memory and attention. Memory is known as the most prominent cognitive domain affected by AD. Clinicians are particularly interested in existing clinically useful NP tests that measure memory impairment at earlier stages of AD. Across the wide variety of NP tests used today for clinical evaluation of AD patients, the Paired Associate Learning (PAL) test developed as part of the *Cambridge Neuropsychological Test Automated Battery* (CANTAB) is known to be very sensitive to detecting memory impairment at earlier stages of AD [Fowler, K. S., Saling, M. M., Conway, E. L., Semple, J. M., & Louis, W. J. (1997). Computerized neuropsychological tests in the early detection of dementia: Prospective findings. Journal of the International Neuropsychological Society, 3, 139-146; Fowler K S, Saling M M, Conway E L, Semple J M, Louis W J: Paired associate performance in the early detection of DAT. J Int Neuropsychol Soc. 2002; 8:58-71.]. CANTAB is a comprehensive, widely used set of NP tests that are administered using a touch screen computer and stylus to improve quantification of behavioural responses.

Figure 7A:
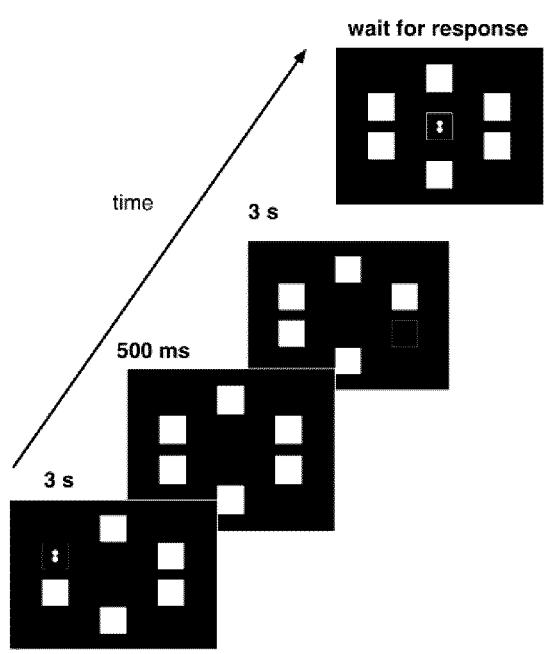
FIGS. 7A-B describe the time evolution of visual stimuli and behavioral responses required during the paired associate learning (PAL) test.
Figure 7B:
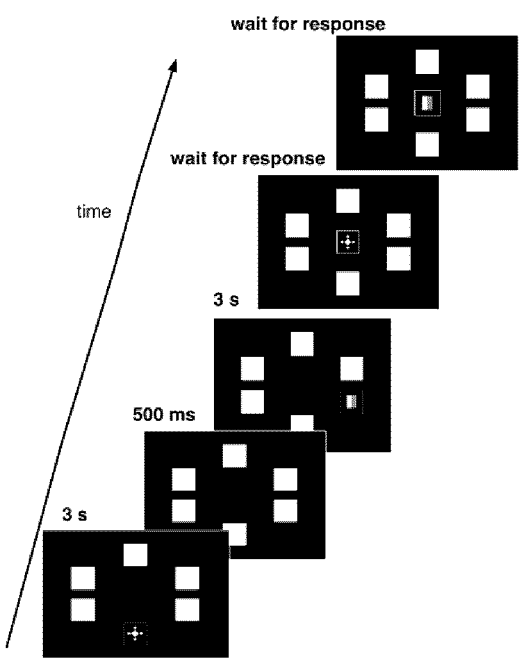
Figure 7C:
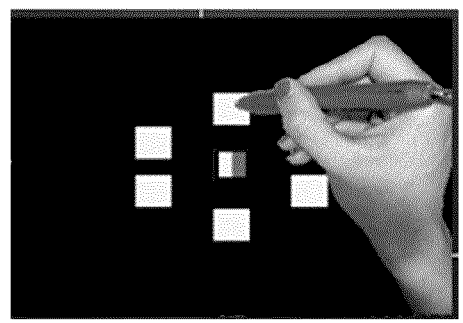
FIG. 7C shows a screen shot of the visual stimulus observed by a subject when performing the PAL test using the tablet with VFHP.

The PAL test probes visual memory and new learning using 6 boxes evenly spaced on a computer touch screen (FIGS. 7A-C). The boxes are opened and closed in random order during the memory "encoding phase". Each box is open for 3 s. One or more boxes contain a pattern. The patterns are then displayed in the middle of the screen, one at a time, and the subject must touch the box where each pattern was originally located (the "recall phase"). If an error is made, the patterns are presented again to remind the subject of their locations. The difficulty level increases through the test from one to six patterns, with six patterns challenging even very able subjects. Examples of the difficulty levels 1 and 2 are shown in FIGS. 7A and 7B, respectively. Scoring consists of the total number of successful and unsuccessful trials.

During the recall phase of the PAL test, the subject is required to touch within one or more small boxes by precise manipulation of the stylus. The complexity of movements increases with increasing task difficulty and the number of patterns to remember. This is potentially concerning in the context of patients who have neurological deficits that impair movement planning and control, confounding assessment of the memory components of the PAL test. For example, when using the tablet without VFHP, it is possible for the patient to select the wrong box when passing over boxes to reach a desired target while pressing the stylus tip on the touch screen. It is also possible to select a box multiple times unintentionally if the stylus remains in contact with the screen on the same location after selecting a box. Hand movement is required to be brief and targeted, which is achievable when using the tablet with VFHP.

In addition to memory impairments, AD patients have shown impaired movement planning during reaching, writing and drawing tasks in the absence of visual feedback of hand position. Visual feedback of hand position while performing complex hand movements is extremely desirable, reducing learning requirements and improving motor performance which could potentially reduce engagement of the sub-network of motor regions during fMRI of the PAL test.

To investigate the influence of VFHP on fMRI tablet measurements, twenty young right-handed healthy adults free from previous or existing neurological impairment performed the PAL test in a 3 T MRI system (MR750, GE Healthcare, Waukesha, Wis.). Ten subjects performed the PAL test with VFHP, and the other ten performed PAL without VFHP. The fMRI setup and procedures were the same as those described in the previous example. The tablet computer was programmed to administer the PAL test as described above with increasing difficulty levels (judgements involving 1, 2, 3, and 6 patterns). A representative example of a subject performing the test is shown in FIG. 7C. The PAL test was repeated 2 times with each difficulty level separated by a 16 s baseline period of visual fixation. Subjects received training on using the touch panel prior to commencement of fMRI. Subjects were instructed to be as accurate and quick as they could at responding. Each collection of encoding for location of patterns, and recall in which subject attempted to touch the box where each pattern was originally located, constituted a single "trial".

It is hypothesized that using the tablet with VFHP to perform the PAL test reduces motor control demands, compared to using the tablet without VFHP. In addition, it is hypothesized that using the tablet with VFHP reduces distraction and attentional demands associated with making tablet responses in the correct locations, allowing more neural resources to be devoted to the visual and memory requirements of the PAL test.

Figure 8A:
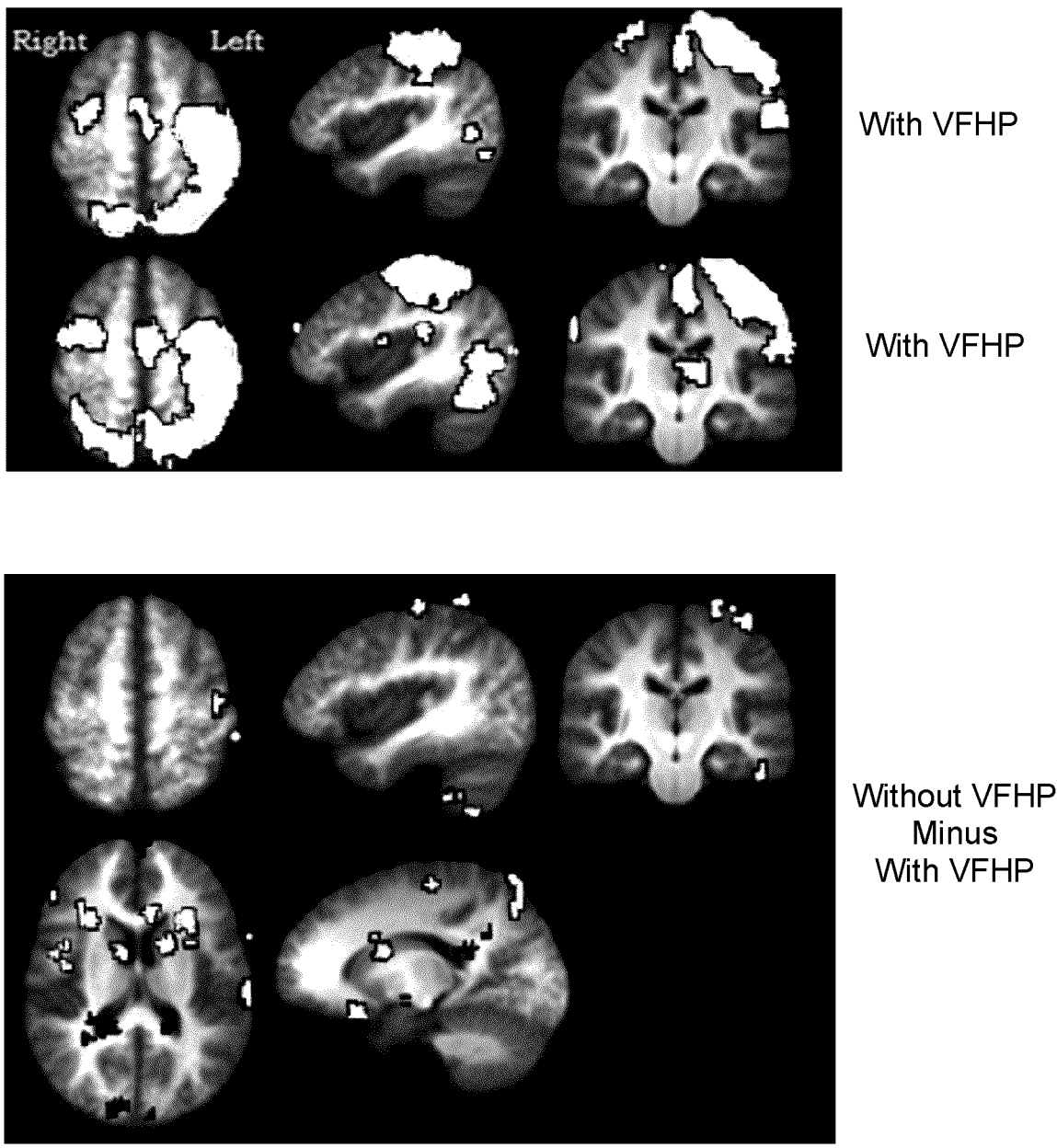
FIG. 8A shows group fMRI data for 10 young healthy subjects performing the PAL test without VFHP and 10 young healthy subjects performing with VFHP. Activation maps are shown for each group for recall phase trials in relation to the rest condition, and the difference in activity between the groups is also provided (Without VFHP versus With VFHP). Brain slices are shown to depict many of the areas involved in controlling movement.

There were no statistically significant differences between the groups in terms of completion time, and contact force when making PAL responses with or without VFHP. Similarly, the two groups showed no statistically significant differences in brain activity across all encoding trials. However, statistically significant differences were observed across all recall trials. FIG. 8 shows these differences in brain activation in specific brain slices, using the same convention for displaying brain activity and brain anatomy as used in FIG. 6A-D. In FIG. 8A, the first row of images shows the average brain activity for all trials of the recall phase of the PAL test contrasted with visual fixation, for subjects using the tablet without VFHP. The next row of images shows the analogous brain activity for subjects using the tablet with VFHP. In both rows, it is evident that there is robust activation of left-lateralized motor control regions associated with making tablet responses during the PAL test. When such activation maps are contrasted to provide a difference map for the two groups of subjects (Without VFHP versus With VFHP), as shown at the bottom of FIG. 8A, statistically significant differences are observed. Subjects using the tablet without VFHP showed more brain activity in cortical motor regions (e.g. pre-central gyrus), as well as subcortical structures such as the bilateral insula and basal ganglia. These increased activations are consistent with subjects in the "without VFHP group" performing a more demanding motor task (i.e. tablet response) than the group of subjects who used the tablet with VFHP.

Figure 8B:
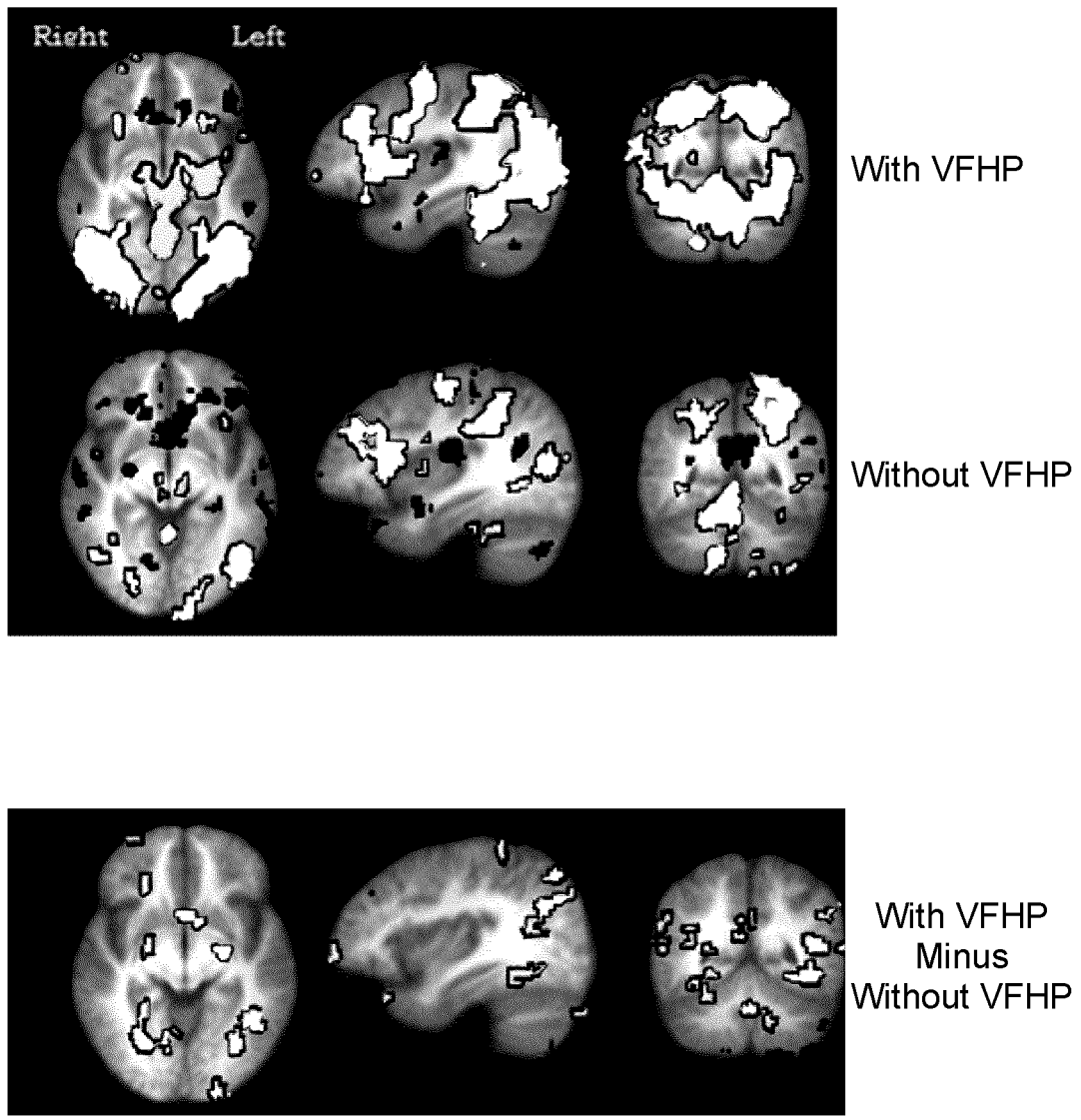
FIG. 8B shows group fMRI data for 10 young healthy subjects performing the PAL test with VFHP and 10 young healthy subjects performing without VFHP. As in FIG. 8A, activation maps are shown for each group for recall phase trials in relation to the rest condition, and the difference in activity between the groups is also provided (With VFHP versus Without VFHP). Brain slices are shown to depict many of the areas involved in visual processing and memory processing that are activated during the PAL test.

FIG. 8B also shows brain activation maps for both groups of subjects for all trials of the recall phase of the PAL test. In this case, brain slices are shown to highlight regions of the occipital lobe and medial temporal lobe that are engaged by the visual and memory components of the test. As in FIG. 8A, the top two rows show average activation maps for each group of subjects and these maps are then contrasted at the bottom of the figure. These data show that subjects using the tablet with VFHP activated occipital and medial temporal lobe structures (e.g. bilateral parahippocampus) to a greater fMRI signal intensity than achieved by subjects using the tablet without VFHP.

The results summarized in FIGS. 7A-C and FIGS. 8A-B suggest that use of the new MRI-compatible tablet with VFHP produces more naturalistic behavioral performance, and that the associated brain activity is more reflective of PAL test performance outside the magnet. During the recall phase of the PAL test, less reliance on proprioception reduces engagement of brain regions responsible for movement processing. Activity in visual regions is larger in extent, associated with increased processing of visual input relevant to task performance. Activity within medial temporal lobe regions is more extensive, consistent with the memory component of the PAL test. The reduced activity associated with motor control, and the increased activity of brain regions engaged in visual and memory processing in subjects using the tablet with VFHP is consistent with performance of the PAL test with less distraction introduced by the demands of making tablet responses. With less mental processing required for tablet responses when there is VFHP, subjects likely are able to devote more neural resources to the cognitive components of the PAL test, which are of primary interest. Although no statistically significant differences in behavioural performance were found between the groups, the differences in brain activity and the arguments provided above suggest that use of the tablet with VFHP is preferable for healthy adults and also for patients that have neurological deficits, especially those involving motor control or attention. In the case of patients suspected of having early AD or its putative precursor, mild cognitive impairment, using the tablet with VFHP would likely provide improved behavioural performance and enhanced ability to map brain activity of pertinent cognitive brain areas while decreasing the likelihood of confounds associated with interacting with the tablet. It is also noteworthy that the results observed in this example likely extend to usage of the tablet with VFHP for fMRI of a wide variety of NP tests.

Example 4

Use of Touch Panel Input with Visual Feedback for fMRI Assessment of Neurosurgical Procedures This example relates to exemplary data acquired during a small clinical trial investigating the utility of HIFU thermal therapy applied to patients with essential tremor. This study was conducted using the same MRI system described in Example 2 outfitted with specialized commercially available HIFU brain surgery apparatus (Insightec, Israel). One representative essential tremor patient was assessed using the touch panel during pre-surgical planning and after therapy was completed. Due to limited time availability for this very preliminary patient testing, the touch panel described in Example 1 was used in the "without visual hand feedback" condition.

Figure 9A:
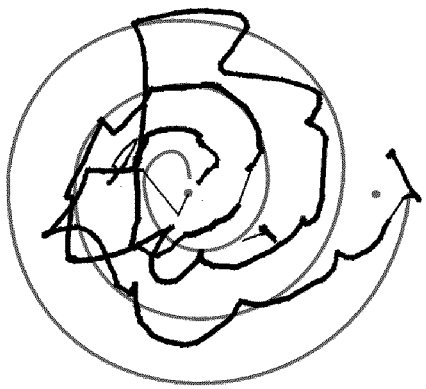
FIGS. 9A-9D show performance on spiral and straight line drawing tasks prior to (FIGS. A and 9C) and after (FIGS. 9B and 9D) a patient with essential tremor is treated using MR-guided high intensity focused ultrasound.
Figure 9B:
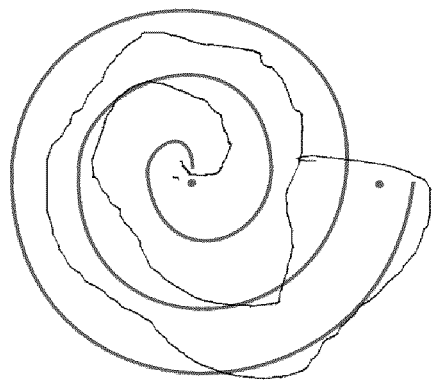
Figure 9C:
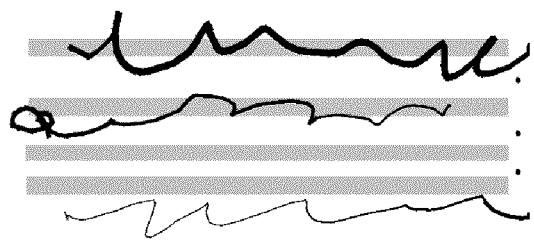

FIGS. 9A-D shows the ability of the patient with essential tremor to perform line-drawing tasks with the tablet pre- and post-MR-guided HIFU treatment. Prior to treatment, the patient exhibited poor performance in drawing spiral and straight lines within bounding guides (FIGS. 9A and 9C).

Figure 9D:
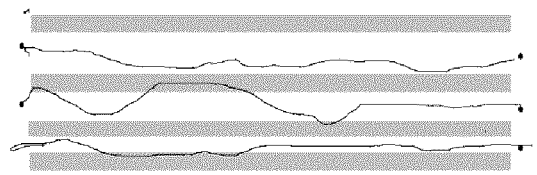

Post-therapy, there was substantially improved performance with line drawing contained mostly within the guides (FIGS. 9B and 9D). Additionally, the post-therapy lines were smoother, with less undulation, and the thickness of the lines representing the drawing force were less variable.

FIG. 9 highlights the potential utility of the present systems and methods during MR-guided diagnostics and/or neuro-therapeutics. In the example shown, involving a patient with essential tremor, impairment of the sensorimotor system is profound and significantly impacts quality of life for aspects of daily living such as eating, drinking, writing and drawing. Tremor is worsened when such patients must move in the real world in the absence of visual feedback (eyes closed); tremor can be reduced to some extent with eyes open. The inclusion of VFHP may thus be beneficial for use with such patients in the future when performing MRI with input provided by a touch panel. This may be important when using the tablet for behavioural assessments either prior to or during MR-guided diagnostics and/or neuro-therapeutics, enabling the patient to improve their ability to sustain contact with the touch-screen surface during tremor. For greater clarity, use of the tablet with VFHP may enable at least some level of behavioural performance to be recorded in some situations, thus avoiding a "floor effect" (lack of task sensitivity due to complete inability to perform the task at all). This is of importance for the intended application of utilizing the touch panel to monitor line-drawing performance intermittently in real-time throughout the entire period of MR-guided intervention. The ability to quickly assess behavioural performance with multiple different tasks could enable improved targeting and treatment of specific intended regions in the brain, while ensuring that surrounding areas of normal brain tissue are not treated, thus minimizing behavioural side effects of the treatment. Behavioural analysis could be performed either semi- or completely-automatically during treatment, with the goal of improving the quality of treatment and reducing treatment time. These benefits are envisaged across the spectrum of MR-guided neuro-interventions (e.g. thermal therapy applications involving high intensity focused ultrasound, laser, microwave, radiofrequency, and cryogenic devices; localized drug delivery with implanted probes or injectable agents localized by ultrasound-mediated disruption of the blood brain barrier) and the spectrum of patient populations to which they are applied (e.g. stroke, neurodegenerative disease, brain cancer, traumatic brain injury). An additional example application involves fMRI evaluation of appropriate placement and pulse generator parameters for patients with deep brain stimulation implants.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of providing visual feedback to a subject during magnetic resonance imaging, wherein the visual feedback is associated with input provided to a touch panel, the method comprising:
   recording input provided by the subject to a magnetic resonance imaging compatible touch panel while the subject is positioned within a magnetic resonance imaging scanner;
   recording, with a video camera, video images of the interaction between the subject and the touch panel while the subject resides within the magnetic resonance imaging scanner, such that the video images include one or more hands of the subject;
   processing the video images and the input provided to the touch panel to generate a real-time video signal comprising:
      a rendering of the input provided to the touch panel by the subject; and
      an image of the one or more hands, showing a real-time position of the one or more hands relative to the input provided to the touch panel; and
   displaying the real-time video signal on a display device viewable by the subject in real time while the subject resides within the magnetic resonance imaging scanner, thereby providing the subject with visual feedback of the real-time position of the one or more hands relative to the input provided to the touch panel.

2. The method according to claim 1 further comprising recording one or more magnetic resonance images of the subject while recording the input from the subject.

3. The method according to claim 1 further comprising:
   receiving, in real-time, in addition to the video images, a measurement of a force applied by the subject to the touch panel; and
   rendering the input in the real-time video signal according to the measured force.

4. The method according to claim 3 wherein the thickness of a line drawn by the subject is rendered in real-time according to the measured force.

5. The method according to claim 3 wherein the duration during which a given pixel is displayed is associated with the force applied to the touch panel at a location of the given pixel.

6. The method according to claim 3 further comprising:
   recording the force as a function of time, thereby obtaining a time-dependent measured force; and
   processing the time-dependent measured force to compute one or more measures.

7. The method according to claim 6 wherein the one or more measures include one or more of: a total non-contact time, a total contact time, a percentage of contact vs. non-contact time, and an average applied force when entering input.

8. The method according to claim 6 wherein the time-dependent measured force is employed as a covariate of interest for modelling brain activity based on functional magnetic resonance images.

9. The method according to claim 1 wherein the input is provided by a stylus held by the subject, and wherein the video signal further comprises an image of the stylus showing a real-time position of the stylus relative to the touch panel.

10. The method according to claim 9 further comprising:
    processing the video images to determine an orientation of the stylus relative to the touch panel; and
    rendering the input in the real-time video signal according to the orientation of the stylus.

11. The method according to claim 9 wherein the input associated with the stylus is recorded, in addition to the video images, when a force applied between the stylus and the touch panel exceeds a pre-selected force threshold.

12. The method according to claim 11 wherein the pre-selected threshold is associated with a given patient population to which the subject belongs.

13. The method according to claim 9 wherein the stylus is rendered in the real-time video signal to have a different geometry than the stylus employed by the subject.

14. The method according to claim 1 wherein processing the video images and generating a frame of the video signal comprises:
   processing a recorded video image to segment and extract, from the recorded image, image data associated with the one or more hands;
   generating an image of the input provided to the touch panel; and
   superimposing an image of the one or more hands with the image of the input provided to the touch panel.

15. The method according to claim 14 wherein the image data is segmented according to one or more fiducial markers provided on a glove worn by the subject.

16. The method according to claim 1 further comprising:
   processing the input provided by the subject to the touch panel; and
   computing one or more measures associated with the input.

17. The method according to claim 16 further comprising associating one or more of the measures with a biomarker.

18. The method according to claim 1 wherein the visual feedback is provided during a therapeutic procedure, the method further comprising measuring one or more magnetic resonance images while recording input from the subject.

19. The method according to claim 18 wherein the visual feedback is employed to provide real-time verification of the therapeutic procedure.

20. The method according to claim 1 wherein the real-time video signal includes an image of at least a portion of the touch panel.

21. The method according to claim 1 wherein the recorded video images, and the real-time video signal, include both of the subject's hands.

22. The method according to claim 1 wherein the image of the one or more hands is partially transparent.

23. A system for providing visual feedback to a subject during functional magnetic resonance imaging, the system comprising:
   a magnetic resonance imaging scanner;
   a magnetic resonance imaging compatible touch panel configured to receive input from the subject while the subject is positioned within said magnetic resonance imaging scanner;
   a video camera positioned and oriented to obtain images of the interaction between the subject and the touch panel while the subject resides within the magnetic resonance imaging scanner, such that the images include one or more hands of the subject;
   a display device positioned to be viewable by the subject while the subject resides within the magnetic imaging resonance scanner;
   a processor operatively coupled to said imaging device and said touch panel, wherein said processor is configured to:
      record input provided by the subject to said magnetic resonance imaging compatible touch panel while the subject is positioned within the magnetic resonance imaging scanner;
      record images obtained by said video camera of the interaction between the subject and said touch panel while the subject resides within the magnetic resonance imaging scanner, such that the images include one or more of the subject's hands;
      process the images and the input provided to said touch panel to generate a real-time video signal comprising:
         a rendering of the input provided to the touch panel by the subject; and
         an image of the one or more hands, showing a real-time position of the one or more hands relative to the input provided to the touch panel; and
      deliver the real-time video signal to said display device to provide the subject with visual feedback of the real-time position of the one or more hands relative to the input provided to the touch panel.

24. The system according to claim 23 further comprising:
   a stylus comprising a force sensor, wherein said force sensor is operatively coupled to said processor;
   wherein said processor is further configured to:
      receive, in real-time, a measurement of the force applied by the subject to the touch panel; and
      modify the rendering of the input in the real-time video signal according to the measured force.

* * * * *